(12) United States Patent
Piette et al.

(10) Patent No.: US 9,211,338 B2
(45) Date of Patent: Dec. 15, 2015

(54) COMPOSITION AND METHOD FOR TREATING HPV

(75) Inventors: Marie Piette, Wanze (BE); Brigitte Evrard, Embourg (BE); Isabelle Coïa, Romsée (BE)

(73) Assignees: Universite Libre de Bruxelles, Brussels (BE); Mithra Pharmaceuticals S.A., Liege (BE)

( * ) Notice: Subject to any disclaimer, the term of this patent is extended or adjusted under 35 U.S.C. 154(b) by 0 days.

(21) Appl. No.: 14/232,529

(22) PCT Filed: Jul. 13, 2012

(86) PCT No.: PCT/EP2012/063796
§ 371 (c)(1),
(2), (4) Date: Jan. 13, 2014

(87) PCT Pub. No.: WO2013/010942
PCT Pub. Date: Jan. 24, 2013

(65) Prior Publication Data
US 2014/0170219 A1    Jun. 19, 2014

Related U.S. Application Data

(60) Provisional application No. 61/508,473, filed on Jul. 15, 2011.

(30) Foreign Application Priority Data

Jul. 15, 2011   (EP) ..................................... 11174193

(51) Int. Cl.
| | | |
|---|---|---|
| *A61K 9/14* | (2006.01) | |
| *A61K 47/38* | (2006.01) | |
| *A61K 9/00* | (2006.01) | |
| *A61K 9/19* | (2006.01) | |
| *A61K 31/675* | (2006.01) | |
| *A61K 9/06* | (2006.01) | |
| *A61K 9/70* | (2006.01) | |

(52) U.S. Cl.
CPC .............. *A61K 47/38* (2013.01); *A61K 9/006* (2013.01); *A61K 9/0014* (2013.01); *A61K 9/0034* (2013.01); *A61K 9/06* (2013.01); *A61K 9/19* (2013.01); *A61K 9/7007* (2013.01); *A61K 31/675* (2013.01)

(58) Field of Classification Search
CPC ... A61K 9/0014; A61K 9/0034; A61K 9/006; A61K 9/7007; A61K 9/19; A61K 31/675; A61K 9/06; A61K 47/38
See application file for complete search history.

(56) References Cited

U.S. PATENT DOCUMENTS

2001/0018072 A1*  8/2001  Unger ........................... 424/484
2005/0276842 A1* 12/2005  Zhang et al. .................. 424/448
2007/0036834 A1*  2/2007  Pauletti et al. ................ 424/426

FOREIGN PATENT DOCUMENTS

EP      1837020 A1   9/2007
WO  2013010942 A1   1/2013

OTHER PUBLICATIONS

International Preliminary Report on Patentability of International Application No. PCT/EP2012/063769, issued Jan. 21, 2014, 12 pages.
International Search Report of International Application No. PCT/EP2012/063769, mailed Oct. 16, 2012, 3 pages.
Collette, D. C., et. al., "Novel Treatment of Atypical Human Papillomavirus-Associated Epithelial Hyperplasia With Cidofovir," Jounal of Oral and Macillofacial Surgery, vol. 69, No. 9, Sep. 2011, pp. 2383-2386.
Sonvico, F., et al., "Therapeutic Paint of Cidofovir/Sucralfate Gel Combination Topically Administered by Spraying for Treatment of orf virus Infections," The AAPS Journal, vol. 11, No. 2, Jun. 2009, pp. 242-249.
Van Pachterbeke, C., et al. "Topical treatment of CN 2+ by cidofovir: Results of a phase II, double-blind, prospective, pleacebo-controlled study," Gynecologic Oncology, vol. 115, No, 1 Oct. 2009, pp. 69-74.
Cundy et al., "Bioavailability and metabolism of cidofovir following topical administration to rabbits," Antiviral Research, vol. 35, No. 2, pp. 113-122.
Tan et al., "Synthesis and swelling properties of the scaffold of PEG/HEMA hydrogels," <Functional material>, vol. 39, No. 4, pp. 626-628, 631.

* cited by examiner

*Primary Examiner* — Suzanne Ziska
(74) *Attorney, Agent, or Firm* — TraskBritt, P.C.

(57) ABSTRACT

Described are lyophilized compositions comprising cidofovir, hydroxypropyl methylcellulose (HPMC) or hydroxyethylcellulose (HEC) and, optionally, a plasticizer. In particular, described are such compositions that form a sheet-shaped porous solid matrix. Also described are methods for producing such compositions and their use in treating human papillomavirus (HPV) infections and HPV-associated malignancies, in particular, HPV lesions and cervical cancer.

31 Claims, 31 Drawing Sheets

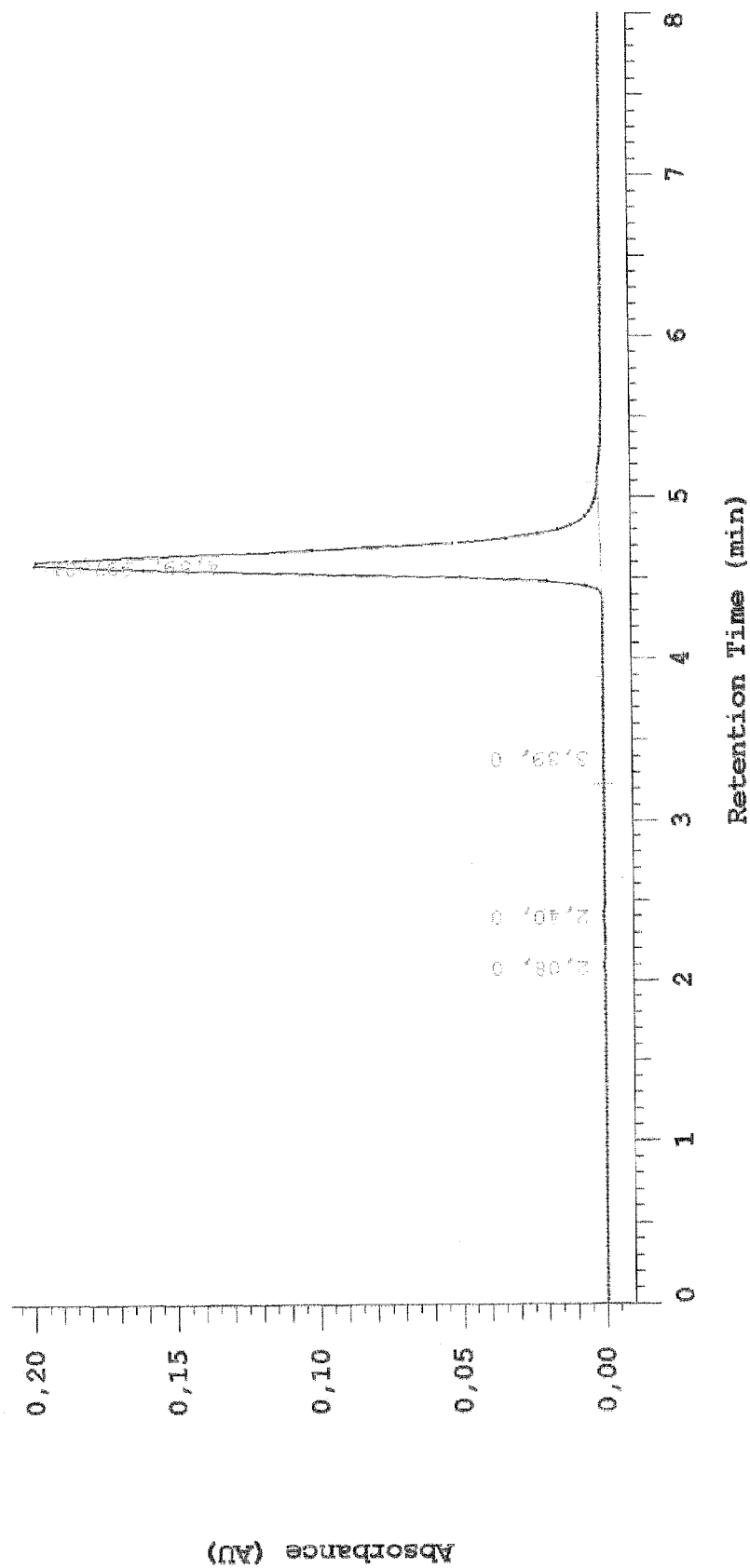

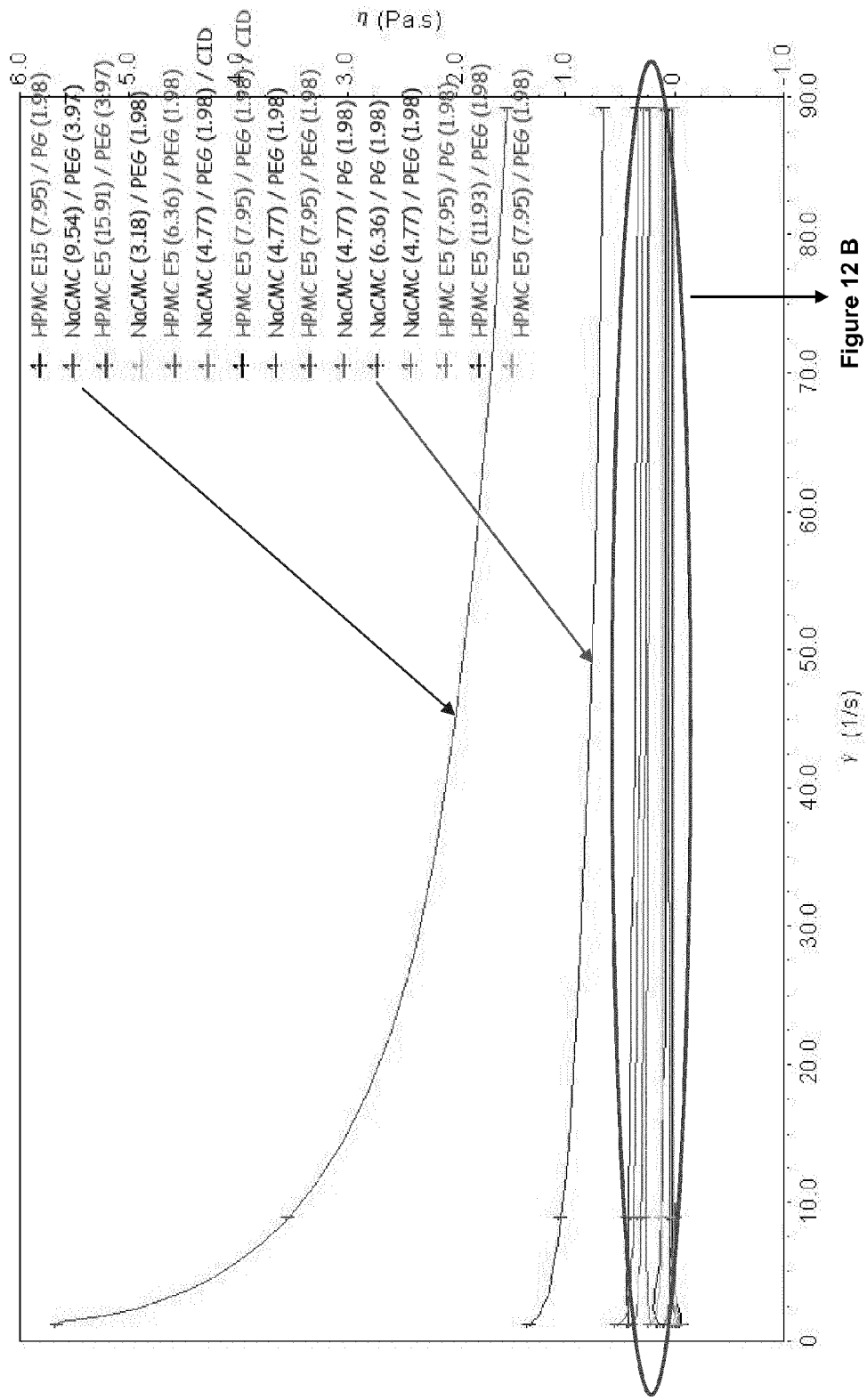

COMPOSITION AND METHOD FOR TREATING HPV

CROSS-REFERENCE TO RELATED APPLICATIONS

This application is a national phase entry under 35 U.S.C. §371 of International Patent Application PCT/EP2012/063796, filed Jul. 13, 2012, designating the United States of America and published in English as International Patent Publication WO 2013/010942 A1 on Jan. 24, 2013, which claims the benefit under Article 8 of the Patent Cooperation Treaty and under 35 U.S.C. §119(e) to European Patent Application Serial No. 11174193.0, filed Jul. 15, 2011, and to U.S. Provisional Patent Application Ser. No. 61/508,473, filed Jul. 15, 2011.

TECHNICAL FIELD

The present disclosure relates to the treatment of viral infections. In particular, this disclosure relates to formulations for treating human papillomavirus (HPV) infections and associated malignancies. The present disclosure specifically relates to solid dosage forms for general drug delivery, topical application or mucosal delivery.

BACKGROUND

DNA viruses such as Herpes, Pox, Papillomavirus, Adenoviruses, Smallpox viruses, etc., can cause many different infectious diseases in humans. One example, Human papillomavirus (HPV), is a member of the papillomaviridae family of non-enveloped DNA viruses capable of infecting humans. Like all papillomaviruses, HPV is strictly epitheliotropic and establishes productive infections only in the stratified epithelium of the skin or mucous membranes. While the majority of the nearly 200 known types of HPV cause no symptoms in most people, some types can cause warts, while others can lead to various cancers, most notably cervical cancer.

More than 30 to 40 types of HPV are typically transmitted through sexual contact and infect the anogenital region. Some sexually transmitted HPV types may cause genital warts. Persistent infection with "high-risk" HPV types, different from the ones that cause skin warts, may progress to precancerous lesions and invasive cancer. HPV infection is a cause of nearly all cases of cervical cancer; however, most infections with these types do not cause disease.

Most HPV infections in young females are temporary and have little long-term significance. 70% of infections are gone in 1 year and 90% in 2 years. However, when infection persists (in 5% to 10% of infected women), there is high risk of developing cervical precancer (lesions on the cervix), which can progress to invasive cervical cancer. This process usually takes 15-20 years, providing many opportunities for detection and treatment of the pre-cancerous condition, often with high cure rates.

While vaccination is an effective way to prevent HPV infection, therapeutic options are limited, expensive and often not well tolerated. Classical therapeutic approaches comprise cytodestructive and cytotoxic substances, surgical methods, laser and cryotherapy, possibly in combination with immunotherapy. In recent years, the acyclic nucleoside phosphonate cidofovir has proven to be effective in the treatment of a variety of clinical manifestations of several DNA viruses such as Herpes, Pox, Papillomavirus, Adenoviruses, Smallpox viruses, etc., in particular, cidofovir has been used to treat HPV-induced epithelial cell proliferation. In vitro treatment of HPV-positive cells with cidofovir has resulted in a concentration- and time-dependent inhibition of cell proliferation. Different parameters of apoptosis showed that the mechanism of cell death following treatment with cidofovir is based on apoptosis. Treatment with intravenous (systemic) cidofovir has been shown to result in the stabilization of disseminated papillomatosis. Local intratumor injections of cidofovir in patients with papillomatous lesions have been shown to result in a complete regression of the tumor. In addition, cidofovir topical gel has been successfully used for the treatment of severe, relapsing anogenital HPV lesions and cervical intraepithelial neoplasia. As cidofovir has been proven to be able to induce apoptosis, the regression of papillomatous tumors may be due, at least in part, to the induction of apoptosis by cidofovir.

As illustrated above, various formulations and routes of administration are presently used for the application of cidofovir. However, each application is presented with specific drawbacks. Systemic administration of an aqueous cidofovir solution, by intravenous injection, possibly leads to systemic side effects. Cidofovir concentrations need to be increased to assure adequate cidofovir amounts at the target site, which may result in nephrotoxicity. On the other hand, local injections of cidofovir at the target site may require multiple injections to assure adequate coverage of the target site. As an alternative to aqueous solutions of cidofovir for injection, creams, gels and films have been developed for topical applications, which may assure localized application to the target site. However, the stability of cidofovir in creams is low and its activity, therefore, deteriorates fast. In addition, the preparation of films includes a heating step, which may entail a risk of heat-mediated cidofovir degradation.

DISCLOSURE

After having performed extensive research, the inventors have found that specific formulations comprising a lyophilized composition comprising cidofovir, hydroxyethylcellulose (HEC) or hydroxypropylmethylcellulose (HPMC) and, optionally, a plasticizer, present a valuable and advantageous alternative for the existing cidofovir formulations.

Therefore, in an aspect, this disclosure relates to a sheet-shaped lyophilized composition comprising:
  (a) cidofovir in an amount between 0.1 and 5.0 mg/cm$^2$;
  (b) hydroxyethylcellulose (HEC) or hydroxypropylmethylcellulose (HPMC) in an amount between 1.0 and 17.0 mg/cm$^2$; and, optionally,
  (c) a plasticizer in an amount between 0 and 5.0 mg/cm$^2$.

In a preferred embodiment, the lyophilized composition according to this disclosure comprises:
  (a) cidofovir in an amount between 0.1 and 5 mg/cm$^2$, preferably between 2.0 and 5.0 mg/cm$^2$;
  (b) HEC in an amount between 1.0 and 17.0 mg/cm$^2$, preferably between 7.0 and 10.5 mg/cm$^2$; and
  (c) a plasticizer in an amount between 0.5 and 4.0 mg/cm$^2$.

Preferably, the HEC is selected from the group consisting of: HEC H4000, HEC 250M, HEC 250HX and HEC 250HHX, most preferably, HEC 250M or HEC 250 HX.

In other preferred embodiments, the lyophilized composition according to this disclosure comprises:
  (a) cidofovir in an amount between 0.1 and 5 mg/cm$^2$;
  (b) HPMC in an amount between 1.0 and 17.0 mg/cm$^2$; and
  (c) a plasticizer in an amount between 0.0 and 5.0 mg/cm$^2$.

Preferably, the HPMC is selected from the group consisting of HPMC E5, HPMC E15, HPMC 4000 and HPMC K15, most preferably, HPMC E5, or HPMC E15.

The inventors have surprisingly found that such formulations form, after lyophilization, a dry, solid, easy to manipulate and malleable porous matrix, which presents itself as a sponge-like structure.

In contrast to the previously known creams or gels, the composition disclosed herein displays excellent cidofovir stability. Hence, and advantageously, the compositions according to this disclosure can be stored at ambient (room) temperature, in contrast to gels and creams, which need to be stored refrigerated.

Moreover, in contrast to the preparation of films, a heating step is absent during the preparation of the compositions disclosed herein, thereby eliminating the risk of heat-mediated cidofovir degradation.

The addition of a small amount of water to the lyophilized composition according to the present disclosure allows for the rapid transformation of the sponge-like structure into a mucoadhesive gel without the need for agitation. It has been found that the speed of rehydration, as well as the quantity of water needed for rehydration, can easily be modulated by changing the type and the concentration of the polymer. In particular, it has been found that the speed of rehydration decreases with increasing concentration of the polymer. Depending on whether a slow rehydration is needed (e.g., for slow release applications) a higher concentration of the polymer can be used in the compositions according to this disclosure. The inventors applicants have also found that HPMC-based sponges require a lower amount of water for rehydration than HEC-based sponges, which might influence the mode of administration. HPMC-based sponges may be administered directly, i.e., without being rehydrated before application. Rehydration may take place in situ, in the uterus, with the aid of a minimal amount of vaginal fluids. This is especially true for HPMC E5, HPMC E15, HPMC 4000 and HPMC K15, most particularly for HPMC E5, and HPMC E15.

The HEC-based sponges on the other hand may be rehydrated prior to administration, resulting in a gel-like composition, which can subsequently be applied into the vagina or cervix of the subject. Rehydration of the HEC-based compositions of this disclosure can be done with a larger quantity of water than for the HPMC-based compositions.

It has further been found that the viscosity of the gel that is obtained after rehydration of the compositions according to this disclosure is determined by the type and the concentration of the polymer (not by the type or the concentration of the plasticizer). This allows for easy modulation of the viscosity depending on the needs by changing the type and concentration of the polymer. In particular, the inventors have found that using the same conditions and amounts of components, the HEC-based sponges are more viscous after rehydration than HPMC-based sponges and present themselves as gels. This is especially true for HEC H4000, HEC 250M, HEC 250HX and HEC 250HHX, most particularly for HEC 250M and HEC 250 HX.

The differences in viscosity are important in determining the way of applying the composition of this disclosure to the subject. The advantage of the HPMC-based compositions, being less viscous, is that less water is needed for the in situ formation of a gel-like structure. They can, therefore, be easily applied internally to the subject without the need for addition of water to invoke rehydration. Rehydration will take place in situ in the body cavity of the subject, using bodily fluids. The HEC-based compositions are more viscous and have the advantage to form a gel, which can be more easily applied topically to, e.g., the anogenital region.

The disclosure, therefore, also provides a gel-like composition obtained after rehydration of the lyophilized compositions according to the disclosure, especially of the HEC-based lyophilized compositions according to this disclosure.

In an embodiment, the plasticizer in the lyophilized composition according to the disclosure, if present, is selected from the group consisting of polyethylene glycol 400 or 4000 (PEG 400 or 4000) and propylene glycol (PG). In a preferred embodiment, the plasticizer in the composition according to the disclosure, if present, is PEG, more preferably PEG 400.

In another embodiment, the lyophilized composition according to the disclosure further comprises water in an amount between 1 and 10 weight %, preferably between 1 and 8 weight %.

In an embodiment, the lyophilized composition according to the disclosure further comprises NaOH. NaOH is generally added to the composition before lyophilization in order to promote the solubilization of cidofovir. In a further embodiment, the compositions according to the disclosure have a pH between 6 and 8, preferably between 6.5 and 7.5 before lyophilization and after rehydration of the matrix.

Preferably, the HPMC in the compositions according to the disclosure is selected from the group consisting of HPMC E5, HPMC E15, HPMC 4000 and HPMC K15; the HEC in the compositions according to the disclosure is selected from the group consisting of: HEC H4000, HEC 250M, HEC 250HX and HEC 250HHX.

The applicants have shown that in contrast to lyophilized placebo compositions comprising various cellulose derivatives such as HPMC, NaCMC, or HEC, which all form malleable sponges, only HPMC- and HEC-based compositions are capable of forming malleable sponges after lyophilization when cidofovir is added.

Unexpectedly, other tested compositions, based on other polymers, such as NaCMC, Carbomer 974P or HPC in the presence of cidofovir do either not form malleable sponges, or present other unfavorable characteristics, such as being very rigid and/or brittle, being too sticky or not adherent at all, showing structural defects or show slow or difficult rehydration. The applicants have shown that the addition of cidofovir alters the structural and functional characteristics of the lyophilized sponges. Furthermore, it has been shown that the addition of cidofovir in the compositions according to the disclosure alters the pore structure of the sponge, in comparison with placebo sponges. In particular, it was found that cidofovir seems to weaken the pore structure, especially in the case of the HPMC-based compositions.

In one aspect, this disclosure relates to the lyophilized composition as described herein for use in topical drug delivery, especially for treating all pathologies linked to infections with human DNA viruses, such as Herpes, Pox, Papillomavirus, Adenoviruses, Smallpox viruses, preferably by HPV, CMV, BK virus, Smallpox, HSV, or VZV, or accompanying pathologies such as those selected from the group comprising: virus-induced lesions or warts of the vagina, cervix, anogenital region, mucosa, epithelium of the oral sphere, or skin, precancerous lesions and/or neoplasms or cancers caused by viral infection, more specifically to the cervix or the mucosal surface of the cervix. In particular, HPV infections and pathologies are envisaged. The term "pathologies linked to HPV or DNA virus infections" encompasses, but is not limited to: HPV or DNA virus-induced lesions or warts of the cervix, uterus, anogenital region, or skin, precancerous lesions and/or neoplasms or cancers caused by HPV or DNA virus infection, more specifically to the cervix or the mucosal surface of the cervix. In another aspect, this disclosure relates to the lyophilized composition as described herein for use in treating human papillomavirus (HPV) infection. In yet another aspect, this disclosure relates to the lyophilized composition as described herein for use in treating cervical cancer. The disclosure described herein also provides for methods of treating HPV or DNA virus infection, using the lyophilized compositions according to the disclosure. Administration of the compositions can be done directly, by inserting the lyophilized composition into the cervix, e.g., on a vaginal inserter or fixed to a vaginal or uteral cap. Alternatively, the composition according to the present disclosure can be rehydrated prior to its administration and subsequently in the cervix applied as a gel-like composition. The treatment can be repeated a number of times in order to prevent, reduce or eliminate the pathologies linked to HPV or DNA virus infections as defined herein, more in particular, HPV or DNA virus infections, or HPV or DNA virus-induced lesions, precancerous lesions, or cancers, especially cervical cancer.

In a further aspect, the disclosure relates to methods for producing the lyophilized composition as described herein, comprising the steps of:
(a) dispersing a polymer in water to obtain a homogenized composition;
(b) optionally dispersing a plasticizer in the composition obtained in step (a) to obtain a homogenized composition;
(c) dispersing cidofovir and optionally adding NaOH 2M solution in the composition obtained in step (b) or, alternatively, the composition obtained in step (a) if no plasticizer is added to obtain a homogenized composition;
(d) lyophilizing the composition obtained in step (c).

In a preferred embodiment of the method of the disclosure:
(a) cidofovir is added in an amount between 0.1 and 5.0 mg/cm$^2$;
(b) hydroxyethylcellulose (HEC) or hydroxypropylmethylcellulose (HPMC) is added in an amount between 1.0 and 17.0 mg/cm$^2$; and, optionally,
(c) a plasticizer is added in an amount between 0 and 5.0 mg/cm$^2$, wherein between 0.5 and 4.0 mg/cm$^2$ of the plasticizer is present when HEC is used.

In a particularly preferred embodiment of the method according to the disclosure:
(a) cidofovir is added in an amount between 0.1 and 5 mg/cm$^2$, preferably between 2.0 and 5.0 mg/cm$^2$;
(b) HEC is added in an amount between 1.0 and 17.0 mg/cm$^2$, preferably between 7.0 and 10.5 mg/cm$^2$; and
(c) a plasticizer is added in an amount between 0.5 and 4.0 mg/cm$^2$.

Preferably, the HEC in the compositions according to this disclosure is selected from the group consisting of: HEC H4000, HEC 250M, HEC 250HX and HEC 250HHX, most preferably HEC 250M and 250HX.

In a further embodiment, the homogenized composition obtained in step (c) comprises NaOH in an amount between 0.10 to 0.30 weight %, preferably about 0.20 or 0.21 weight %, before lyophilization.

In other preferred embodiments, the lyophilized composition according to the disclosure comprises:
(a) cidofovir is added in an amount between 0.1 and 5 mg/cm$^2$;
(b) HPMC is added in an amount between 1.0 and 17.0 mg/cm$^2$; and
(c) a plasticizer is added in an amount between 0.0 and 5.0 mg/cm$^2$.

Preferably, HPMC is selected from the group consisting of HPMC E5, HPMC E15, HPMC 4000 and HPMC K15, most preferably HPMC E5 and E15.

In a further embodiment, the homogenized composition obtained in step (c) comprises NaOH in an amount between 0.10 to 0.30 weight %, preferably about 0.20 or 0.21 weight %, before lyophilization.

Preferably, plasticizer is selected from the group consisting of polyethylene glycol 400 or 4000 (PEG 400 or 4000) and propylene glycol (PG). In a preferred embodiment, the plasticizer in the composition according to the disclosure, if present, is PEG, more preferably PEG 400.

In a further embodiment, the homogenized composition obtained in step (c) comprises between 0.35 and 3.5 weight % of HEC or HPMC. In particular embodiments, the homogenized composition obtained in step (c) comprises between 1 and 2.5 weight % HEC and between 0.2 and 1 weight % plasticizer. In other particular embodiments, the homogenized composition obtained in step (c) comprises between 0.35 and 3.5 weight % HPMC and between 0 and 1 weight % plasticizer. In yet another embodiment, the homogenized composition of step (c) comprises between 0.10 and 1.5 weight % cidofovir. In an embodiment, the homogenized composition obtained in step (c) has a pH between 6 and 8, preferably between 6.5 and 7.5.

In a further embodiment, the homogenized composition obtained in step (c) comprises NaOH in an amount between 0.10 to 0.30 weight %, preferably about 0.20 or 0.21 weight %, before lyophilization.

In an embodiment, the lyophilization for producing the compositions according to the disclosure can be performed in a crystallizer, or in a mold, or in any other known device or reactor that can be used to make a sheet-like lyophilized composition of the disclosure described herein.

Another aspect of this disclosure relates to a sheet-shaped solid porous malleable matrix obtained by lyophilization of an aqueous composition, the aqueous composition comprising between 0.35 and 3.5 weight % HEC or HPMC, between 0 and 1 weight % plasticizer, and between 0.10 and 1.5 weight % cidofovir.

In particular embodiments, this matrix comprises between 1 and 2.50 weight % HEC, between 0.2 and 1 weight % plasticizer, and between 0.10 and 1.5 weight % cidofovir.

In other particular embodiments, this matrix comprises between 0.35 and 3.50 weight % HPMC, between 0 and 1 weight % plasticizer, and between 0.10 and 1.5 weight % cidofovir.

In an embodiment, this matrix comprises between 1 and 17 mg/cm$^2$ HEC or HPMC, between 0 and 5 mg/cm$^2$ plasticizer, and between 0.1 and 5 mg/cm$^2$ cidofovir.

In particular embodiments, this matrix comprises between 7 and 10.5 mg/cm$^2$ HEC, between 1.5 and 5 mg/cm$^2$ plasticizer, and between 0.1 and 5 mg/cm$^2$ cidofovir, preferably with HEC 250M or HEC 250HX as the polymer.

In other particular embodiments, this matrix comprises between 1 and 17 mg/cm$^2$ HPMC, between 0 and 5 mg/cm$^2$ plasticizer, and between 0.1 and 5 mg/cm$^2$ cidofovir, preferably with HPMC E5 or E15 as the polymer.

A further aspect of this disclosure relates to a drug delivery applicator comprising the sheet-shaped lyophilized composition or the malleable matrix according to the disclosure as described herein disposed on a drug-impermeable barrier.

In an embodiment, the drug-impermeable barrier is a cap that is configured to fit over an outer periphery of a cervix.

BRIEF DESCRIPTION OF THE DRAWINGS

(FIG. 1A) chromatogram of calibrated cidofovir; (FIG. 1B)

chromatogram of cidofovir from a lyophilized composition comprising HPMC E5 according to an embodiment of this disclosure at T0; and (FIGS. 1C, 1D, 1E, 1F and 1G) chromatograms of cidofovir from a lyophilized composition according to an embodiment of the disclosure, respectively, at T1, T3, T6, T9 and T12, i.e., after 1, 3, 6, 9 and 12 month(s) of storage at 45° C.

(FIG. 2A) chromatogram of cidofovir from a lyophilized composition comprising HEC 250HX according to an embodiment of the disclosure at T0; and (FIGS. 2B and 2C) chromatograms of cidofovir from a lyophilized composition according to an embodiment of the disclosure at T1 and T3, i.e., after 1 and 3 months of storage at 45° C.

(FIG. 3A) Diffusion kinetics of cidofovir in various lyophilized compositions according to an embodiment of the disclosure (HPMC E5-based) in comparison to carbomer gel (prior art); (FIG. 3B) diffusion kinetics of cidofovir in various NaCMC-based compositions in comparison to carbomer gel (prior art); and (FIG. 3C) diffusion kinetics of cidofovir in various HEC 250M and 250HX-based compositions in comparison to carbomer gel (prior art).

Figure 1A:
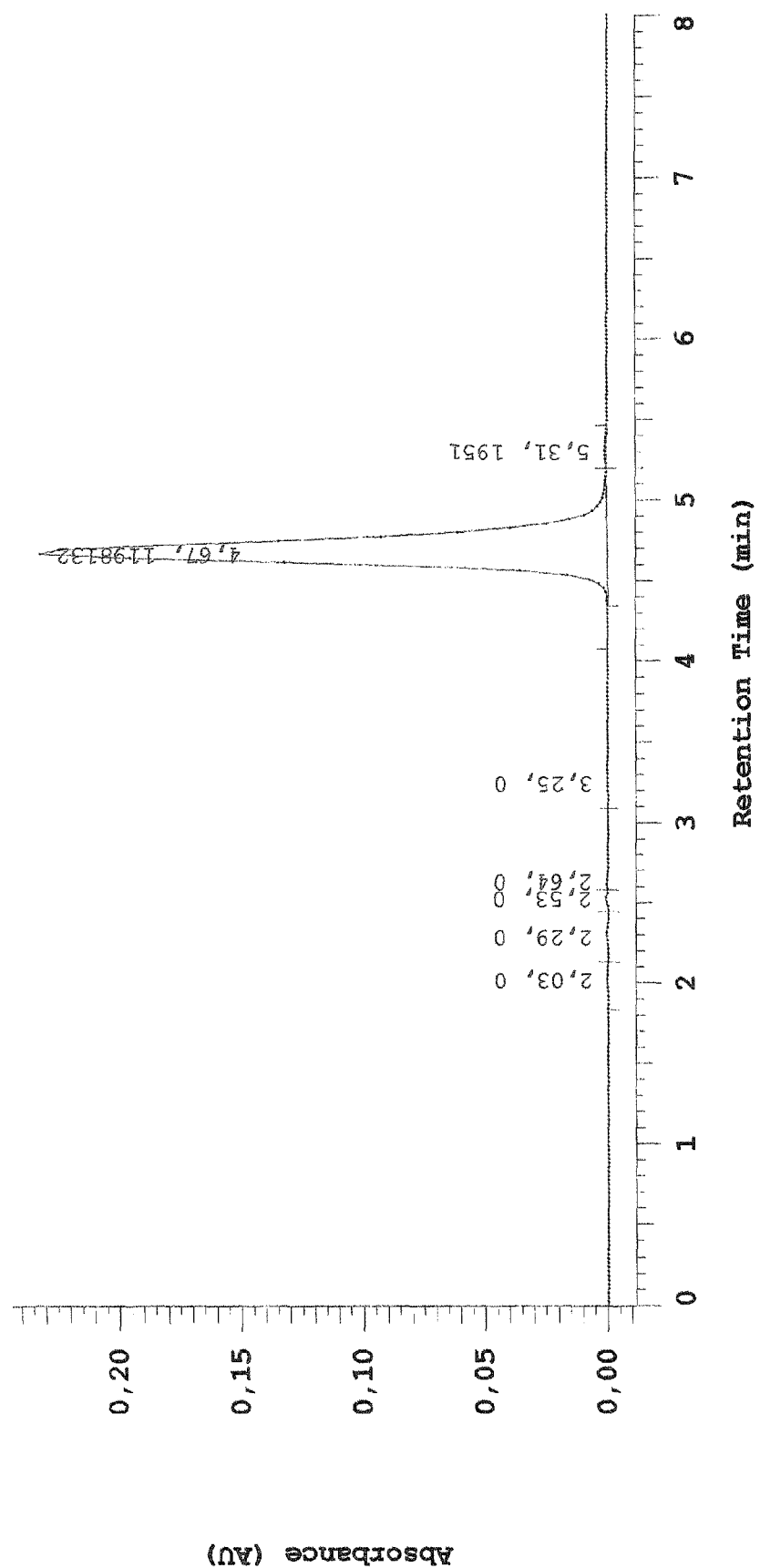
FIGS. 1A-1G: HPLC chromatograms of cidofovir showing absorbance (AU) in function of retention time (minutes).

As used herein, the singular forms "a," "an," and "the" include both singular and plural references unless the context clearly dictates otherwise.

The terms "comprising," "comprises," and "comprised of" as used herein are synonymous with "including," "includes" or "containing," "contains," and are inclusive or open-ended and do not exclude additional, non-recited members, elements or method steps. It will be appreciated that the terms "comprising," "comprises," and "comprised of" as used herein comprise the terms "consisting of," "consists," and "consists of."

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosure described herein. It is to be understood that the value to which the modifier "about" or "approximately" refers is itself also specifically, and preferably, disclosed.

Whereas the teens "one or more" or "at least one," such as one or more or at least one member(s) of a group of members, is clear per se, by means of further exemplification, the term encompasses, inter alia, a reference to any one of the members, or to any two or more of the members, such as, e.g., any ≥3, ≥4, ≥5, ≥6, or ≥7, etc., of the members, and up to all of the members.

All references cited in the present specification are hereby incorporated by reference in their entirety. In particular, the teachings of all references herein specifically referred to are incorporated by reference.

Unless otherwise defined, all terms used in describing the disclosure, including technical and scientific terms, have the meaning as commonly understood by one of ordinary skill in the art to which this disclosure belongs. By means of further guidance, term definitions are included to better appreciate the teaching of the present disclosure.

In the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure, and form different embodiments, as would be understood by those in the art. For example, in the appended claims, any of the claimed embodiments can be used in any combination.

The disclosure relates to a sheet-shaped lyophilized composition comprising:

(a) cidofovir in an amount between 0.1 and 5 mg/cm$^2$;

(b) hydroxyethylcellulose (HEC) or hydroxypropylmethylcellulose (HPMC) in an amount between 1.5 and 17 mg/cm$^2$; and, optionally, (c) a biocompatible plasticizer in an amount between 0 and 5 mg/cm'.

Particularly preferred embodiments of compositions according to the disclosure are listed in Tables A to D. Tables A-D list the concentrations of the excipients after lyophilization in mg/cm$^2$ and before lyophilization in weight % (with HPMC as polymer and without plasticizer in Table A; with HPMC as polymer and with PEG 400 as plasticizer in Table B; with HPMC as polymer and with PG as plasticizer in Table C; with HEC as polymer and PEG 400 as plasticizer in Table D). Values in Tables A to D are indicated with a deviation of ±10% of each specific value (e.g., 3.97 mg/cm$^2$ HPMC E5±10% ranges between 3.97−0.397 mg/cm$^2$ and 3.97+0.397 mg/cm$^2$; 0.42% PEG 400±10% ranges between 0.42−0.042% and 0.42+0.042%).

TABLE A

| | HPMC | | cidofovir | | total weight |
|---|---|---|---|---|---|
| Type | mg/cm$^2$ | % | mg/cm$^2$ | % | g |
| E5 | 3.97 ± 10% | 0.83 ± 10% | 4.77 ± 10% | 1 ± 10% | 6 |
| E5 | 7.95 ± 10% | 1.43 ± 10% | 4.77 ± 10% | 0.86 ± 10% | 7 |
| E5 | 7.95 ± 10% | 1.67 ± 10% | 4.77 ± 10% | 1 ± 10% | 6 |

TABLE B

| | HPMC | | PEG 400 | | cidofovir | | total weight |
|---|---|---|---|---|---|---|---|
| Type | mg/cm$^2$ | % | mg/cm$^2$ | % | mg/cm$^2$ | % | g |
| E5 | 2.45 ± 10% | 1 ± 10% | 0.49 ± 10% | 0.2 ± 10% | 0.36 ± 10% | 0.15 ± 10% | 10 |
| E5 | 3.14 ± 10% | 1 ± 10% | 0.63 ± 10% | 0.2 ± 10% | 0.94 ± 10% | 0.3 ± 10% | 5 |
| E5 | 3.97 ± 10% | 0.83 ± 10% | 1.98 ± 10% | 0.42 ± 10% | 4.77 ± 10% | 1 ± 10% | 6 |
| E5 | 6.36 ± 10% | 1.33 ± 10% | 1.98 ± 10% | 0.42 ± 10% | 4.77 ± 10% | 1 ± 10% | 6 |
| E5 | 7.95 ± 10% | 1.43 ± 10% | 1.98 ± 10% | 0.36 ± 10% | 4.77 ± 10% | 0.86 ± 10% | 7 |
| E5 | 7.95 ± 10% | 1.67 ± 10% | 1.98 ± 10% | 0.42 ± 10% | 4.77 ± 10% | 1 ± 10% | 6 |
| E5 | 7.95 ± 10% | 1.67 ± 10% | 1.98 ± 10% | 0.42 ± 10% | 2.38 ± 10% | 0.5 ± 10% | 6 |
| E5 | 11.93 ± 10% | 2.5 ± 10% | 1.98 ± 10% | 0.42 ± 10% | 4.77 ± 10% | 1 ± 10% | 6 |

TABLE B-continued

| | HPMC | | PEG 400 | | cidofovir | | total weight |
|---|---|---|---|---|---|---|---|
| Type | mg/cm$^2$ | % | mg/cm$^2$ | % | mg/cm$^2$ | % | g |
| E5 | 12.57 ± 10% | 1.67 ± 10% | 2.51 ± 10% | 0.33 ± 10% | 1.88 ± 10% | 0.25 ± 10% | 12 |
| E5 | 15.91 ± 10% | 3.33 ± 10% | 1.98 ± 10% | 0.42 ± 10% | 2.387 ± 10% | 0.5 ± 10% | 6 |
| E5 | 3.97 ± 10% | 0.83 ± 10% | 3.97 ± 10% | 0.83 ± 10% | 4.77 ± 10% | 1 ± 10% | 6 |
| E5 | 6.366 ± 10% | 1.33 ± 10% | 3.97 ± 10% | 0.83 ± 10% | 4.77 ± 10% | 1 ± 10% | 6 |
| E5 | 7.95 ± 10% | 1.67 ± 10% | 3.97 ± 10% | 0.83 ± 10% | 4.77 ± 10% | 1 ± 10% | 6 |
| E5 | 7.95 ± 10% | 1.67 ± 10% | 3.97 ± 10% | 0.83 ± 10% | 2.38 ± 10% | 0.5 ± 10% | 6 |
| E5 | 15.91 ± 10% | 3.33 ± 10% | 3.97 ± 10% | 0.83 ± 10% | 4.77 ± 10% | 1 ± 10% | 6 |
| E15 | 7.95 ± 10% | 1.67 ± 10% | 1.98 ± 10% | 0.42 ± 10% | 4.77 ± 10% | 1 ± 10% | 6 |
| 4000 | 7.95 ± 10% | 1.67 ± 10% | 1.98 ± 10% | 0.42 ± 10% | 4.77 ± 10% | 1 ± 10% | 6 |
| 4000 | 9.54 ± 10% | 2 ± 10% | 1.98 ± 10% | 0.42 ± 10% | 4.77 ± 10% | 1 ± 10% | 6 |
| 4000 | 9.54 ± 10% | 2 ± 10% | 3.97 ± 10% | 0.83 ± 10% | 4.77 ± 10% | 1 ± 10% | 6 |
| K15 | 7.95 ± 10% | 1.67 ± 10% | 1.98 ± 10% | 0.42 ± 10% | 4.77 ± 10% | 1 ± 10% | 6 |

TABLE C

| | HPMC | | PG | | cidofovir | | total weight |
|---|---|---|---|---|---|---|---|
| Type | mg/cm$^2$ | % | mg/cm$^2$ | % | mg/cm$^2$ | % | g |
| E5 | 7.95 ± 10% | 1.67 ± 10% | 1.98 ± 10% | 0.42 ± 10% | 2.38 ± 10% | 0.5 ± 10% | 6 |
| 4000 | 1.98 ± 10% | 0.42 ± 10% | 3.97 ± 10% | 0.83 ± 10% | 2.38 ± 10% | 0.5 ± 10% | 6 |
| K15 | 1.98 ± 10% | 0.42 ± 10% | 3.97 ± 10% | 0.83 ± 10% | 2.38 ± 10% | 0.5 ± 10% | 6 |

TABLE D

| | HEC | | PEG 400 | | cidofovir | | total weight |
|---|---|---|---|---|---|---|---|
| Type | mg/cm$^2$ | % | mg/cm$^2$ | % | mg/cm$^2$ | % | g |
| 250 M | 7.95 ± 10% | 1.67 ± 10% | 1.98 ± 10% | 0.42 ± 10% | 2.38 ± 10% | 0.5 ± 10% | 6 |
| 250 M | 9.54 ± 10% | 2 ± 10% | 1.98 ± 10% | 0.42 ± 10% | 4.77 ± 10% | 1 ± 10% | 6 |
| 250 M | 9.54 ± 10% | 2 ± 10% | 3.58 ± 10% | 0.75 ± 10% | 4.77 ± 10% | 1 ± 10% | 6 |
| 250 HX | 7.95 ± 10% | 1.67 ± 10% | 1.98 ± 10% | 0.42 ± 10% | 4.77 ± 10% | 1 ± 10% | 6 |

In another embodiment, the disclosure provides a pharmaceutical composition comprising a therapeutically effective amount of the lyophilized composition described above and a further pharmaceutically acceptable carrier.

In an aspect of the embodiment, the pharmaceutical composition further comprises an anti-viral agent. The anti-viral agent can be an Interferon, imiquimod, formaldehyde, glutaral, cimetidine, 5-fluorouracil, trichloroacetic acid, bleomycin, podofilox, podophyllum or any other anti-viral composition useful for the treatment of HPV infections, HPV-infected tissue, or HPV-infected cells.

In still another embodiment, the disclosure provides a method of treating HPV infections, HPV-infected tissue or HPV-infected cells comprising contacting the infectious site, infected tissue or cells with the lyophilized composition described herein. In an aspect of the disclosure, the method further comprises contacting the cells with an anti-viral agent. The anti-viral agent can be an Interferon, imiquimod, formaldehyde, glutaral, cimetidine, 5-fluorouracil, trichloroacetic acid, bleomycin, podofilox, podophyllum, or any other anti-viral composition useful for the treatment of HPV infections, HPV-infected tissue, or HPV-infected cells. The anti-viral agent can be comprised in the lyophilized composition of the disclosure, or can be administered simultaneously, prior to, or following the administration of the lyophilized composition according to the present disclosure.

More than 150 types of HPV are acknowledged to exist. Of these, the following have been classified as types involving risk for cervical cancer: HPV-1, 6, 11, 16, 18, 26, 31, 33, 35, 39, 40, 42, 43, 44, 45, 51, 52, 53, 54, 56, 58, 59, 61, 66, 68, 70, 72, 73, 81, 82, and CP6108. Types 16 and 18 are generally acknowledged to cause about 70% of cervical cancer cases. Together with type 31, they are the prime risk factors for cervical cancer. In any of the embodiments described herein, HPV can be HPV 11, HPV16, HPV18, HPV1, HPV6, any further type of HPV listed above, and any combination thereof.

Administration of the lyophilized composition according to the present disclosure, or the pharmaceutical composition as defined herein can be done directly, i.e., without rehydration of the lyophilized matrix, by using, e.g., a vaginal inserter, a tampon inserter, a cervical cap, a cervix-covering pessary, or any other tool that can be used to position the lyophilized matrix at the HPV-infected tissue or cells. In this scenario, the lyophilized structure will be rehydrated in situ, using bodily fluids naturally present at the site of application.

Alternatively, the lyophilized composition according to the present disclosure, or the pharmaceutical composition as defined herein can be rehydrated prior to use, creating a gel-like composition that can be topically applied by using, e.g., a vaginal cream inserter, a tampon inserter, a cervical cap, a cervix-covering pessary or any other tool that can be used to position the gel at the HPV-infected tissue or cells.

According to the disclosure, an "effective amount" of the composition or pharmaceutical composition is that amount effective for treating or lessening the severity of HPV infections.

Typically, HPV infections occur at the skin, mucosa, anogenital region, vulva, vagina, and the cervix (the passage between the vagina and the uterus), in which they may cause lesions, precancerous lesions, genital warts, polyps, cysts, benign neoplasms and eventually cancers, that can metastasis into the underlying tissues and circulate into the blood vessels. Cervical cancer may present with vaginal bleeding, but symptoms may be absent until the cancer is in its advanced stages. In addition, epithelial HPV infections of the oral cavity or sphere are frequently occurring. The oral cavity or sphere encompasses the lips, mouth, throat, larynx, etc. The preferred target sites for the (pharmaceutical) composition according to the present disclosure is, therefore, the vulvar, vaginal, and cervical region, especially the mucosal tissue in these areas, which are most often infected with HPV.

The disclosure will now be illustrated by means of the following examples, which do not limit the scope of this disclosure in any way.

EXAMPLES

Example 1

Lyophilization Conditions

Lyophilization of aqueous compositions comprising a bioadhesive polymer and, optionally, a plasticizer and/or cidofovir to obtain a porous malleable matrix was performed according to the following protocol.

The polymer is dispersed in distilled water under slow agitation until complete homogenization. Optionally, the obtained dispersion is agitated again until complete homogenization after the addition of the plasticizer. Cidofovir is dispersed and a 2 M NaOH stock solution is added to reach pH 7. The obtained mixture is transferred to a crystallizer and is lyophilized. The lyophilization conditions are the following:

Freezing

| Stage | Temperature (° C.) | Time (h) | Pressure (bar) |
|---|---|---|---|
| 1 | −35 (−30 to −35) | 3.0 (2 to 4) | ambient |
| 2 | −35 (−30 to −35) | 0.5 (0.4 to 0.6) | ambient |

Primary Drying

| Stage | Temperature (° C.) | Time (h) | Pressure (bar) |
|---|---|---|---|
| 1 | −15 (−10 to −20) | 3.0 (2 to 4) | 0.8 (0.7 to 0.9) |
| 2 | −10 (−10 to −20) | 12.0 (7 to 17) | 0.1 (0.05 to 0.15) |

Secondary Drying

| Stage | Temperature (° C.) | Time (h) | Pressure (bar) |
|---|---|---|---|
| 1 | 10 (5 to 15) | 2.0 (1 to 3) | 0.1 (0.05 to 0.15) |
| 2 | 10 (5 to 15) | 3.0 (2 to 4) | 0.1 (0.05 to 0.15) |

Example 2

Components of the Lyophilized Composition

The following components and mixtures were evaluated for their capacity to result in the desired "sponge" structure after lyophilization.
  Bioadhesive Polymers:
  Hydroxypropylmethylcellulose (HPMC)
    HPMC E5: viscosity: 5 mPa·s (=5 cp) (aqueous solution of 2%)
    HPMC E15: viscosity: 12-18 mPa·s (aqueous solution of 2%)
    HPMC 4000: viscosity: 4000-5600 mPa·s (aqueous solution of 2%)
    HPMC K15: viscosity: 11250-21000 mPa·s (aqueous solution of 2%)
  Sodium carboxymethyl cellulose (NaCMC)
  Hydroxyethylcellulose (HEC)
    HEC Natrosol 250HX: viscosity: 1500-2500 mPa·s (aqueous solution of 1%)
    HEC Natrosol 250HHX: viscosity: 3500-5500 mPa·s (aqueous solution of 1%)
    HEC Natrosol 250M: viscosity: 4500-6500 mPa·s (aqueous solution of 2%)
    HEC H4000: viscosity: 4500-6500 mPa·s (aqueous solution of 2%)
  Carbomer 974P
  Hydroxyproprylcellulose (HPC)
    HPC LF: viscosity: 75-150 mPa·s (aqueous solution of 5%)
    HPC HF: viscosity: 1500-3000 mPa·s (aqueous solution of 1%)
    HPC GF: viscosity: 150-400 mPa·s (aqueous solution of 2%)
  Plasticizers:
  polyethylene glycol 400 (PEG 400)
  polyethylene glycol 4000 (PEG 4000)
  propylene glycol (PG)

Example 3

Evaluation of Different Lyophilized Placebo Compositions

Different conditions and concentrations of the components were tested to evaluate the desired characteristics of the lyophilisate. Desired characteristics are a sponge texture that is easily malleable when dry and that can be easily and/or rapidly rehydrated into a gel with intermediate viscosity (i.e., not too liquid and not too viscous).

The following conditions were kept constant for ease of comparison: the diameter of the crystallizer (4 cm), the quantity of water used for the dispersion of the components (ad 6 g, meaning water was added to the composition up to 6 g of the final composition before lyophilization), and the lyophilization cycle.

In the first instance, placebo lyophilisates were evaluated (i.e., without cidofovir). Table 1 lists the tested concentrations of polymer and plasticizer.

TABLE 1

| Polymer | mg/cm² | Plasticizer | mg/cm² | remarks |
|---|---|---|---|---|
| HPMC E5 | 3.97 | — | — | malleable sponge |
| HPMC E5 | 7.95 | — | — | malleable sponge |
| HPMC 4000 | 9.54 | — | — | malleable sponge |
| HPMC 4000 | 11.93 | — | — | malleable sponge |
| HPMC E5 | 3.97 | PEG 400 | 1.98 | malleable sponge |
| HPMC E5 | 6.36 | PEG 400 | 1.98 | malleable sponge |
| HPMC E5 | 7.95 | PEG 400 | 1.98 | malleable sponge |
| HPMC E5 | 11.93 | PEG 400 | 1.98 | malleable sponge |
| HPMC E5 | 15.91 | PEG 400 | 1.98 | malleable sponge |
| HPMC E5 | 3.97 | PEG 400 | 3.97 | malleable sponge |
| HPMC E5 | 6.36 | PEG 400 | 3.97 | malleable sponge |
| HPMC E5 | 7.95 | PEG 400 | 3.97 | malleable sponge |
| HPMC E5 | 15.91 | PEG 400 | 3.97 | malleable sponge |
| HPMC E5 | 31.83 | PEG 400 | 7.95 | malleable sponge |
| HPMC E5 | 71.62 | PEG 400 | 7.95 | malleable sponge |
| HPMC E15 | 6.36 | PEG 400 | 1.98 | malleable sponge |
| HPMC E15 | 7.95 | PEG 400 | 1.98 | malleable sponge |
| HPMC 4000 | 3.97 | PEG 400 | 1.98 | malleable sponge |
| HPMC 4000 | 6.36 | PEG 400 | 1.98 | malleable sponge |
| HPMC 4000 | 7.95 | PEG 400 | 1.98 | malleable sponge |
| HPMC 4000 | 9.54 | PEG 400 | 1.98 | malleable sponge |
| HPMC 4000 | 11.93 | PEG 400 | 1.98 | malleable sponge |
| HPMC K15 | 1.98 | PEG 400 | 0.99 | malleable sponge |
| HPMC K15 | 7.95 | PEG 400 | 1.98 | malleable sponge |
| HPMC E5 | 7.95 | PEG 4000 | 0.79 | malleable sponge |
| HPMC E5 | 7.95 | PEG 4000 | 1.19 | malleable sponge |
| HPMC E5 | 7.95 | PEG 4000 | 1.98 | malleable sponge |
| HPMC E5 | 7.95 | PG | 1.98 | malleable sponge |
| HPMC E5 | 7.95 | PG | 3.97 | malleable sponge |
| HPMC E15 | 6.36 | PG | 3.97 | malleable sponge |
| HPMC E15 | 7.95 | PG | 1.98 | malleable sponge |
| HPMC E15 | 11.93 | PG | 3.97 | malleable sponge |
| HPMC 4000 | 1.98 | PG | 1.98 | malleable sponge |
| HPMC 4000 | 3.97 | PG | 1.98 | malleable sponge |
| HPMC K15 | 1.98 | PG | 1.98 | malleable sponge |
| HPMC K15 | 3.97 | PG | 1.98 | malleable sponge |
| NaCMC | 3.18 | PEG 400 | 1.98 | malleable sponge |
| NaCMC | 4.77 | PEG 400 | 1.98 | malleable sponge |
| NaCMC | 5.57 | PEG 400 | 1.98 | malleable sponge |
| NaCMC | 6.36 | PEG 400 | 1.98 | malleable sponge |
| NaCMC | 4.77 | PEG 400 | 3.97 | malleable sponge |
| NaCMC | 9.55 | PEG 400 | 3.97 | malleable sponge |
| NaCMC | 4.77 | PG | 1.98 | malleable sponge |
| NaCMC | 4.77 | PG | 3.97 | malleable sponge |
| HEC H4000 | 9.54 | — | — | malleable sponge |
| HEC H4000 | 11.93 | — | — | malleable sponge |
| HEC H4000 | 9.54 | PEG 400 | 1.98 | malleable sponge |
| HEC H4000 | 11.93 | PEG 400 | 1.98 | malleable sponge |
| HEC H4000 | 11.93 | PEG 400 | 3.97 | malleable sponge |
| HEC 250 M | 9.54 | — | — | malleable sponge |
| HEC 250 M | 11.93 | — | — | malleable sponge |
| HEC 250 M | 3.97 | PEG 400 | 1.98 | malleable sponge |
| HEC 250 M | 4.77 | PEG 400 | 1.98 | malleable sponge |
| HEC 250 M | 7.95 | PEG 400 | 1.98 | malleable sponge |
| HEC 250 M | 9.54 | PEG 400 | 1.98 | malleable sponge |
| HEC 250 M | 11.93 | PEG 400 | 1.98 | malleable sponge |
| HEC 250 M | 11.93 | PEG 400 | 3.97 | malleable sponge |
| HEC 250 HX | 7.16 | — | — | malleable sponge |
| HEC 250 HX | 7.95 | — | — | malleable sponge |
| HEC 250 HX | 11.93 | — | — | malleable sponge |
| HEC 250 HX | 3.97 | PEG 400 | 1.98 | malleable sponge |
| HEC 250 HX | 7.95 | PEG 400 | 1.98 | malleable sponge |
| HEC 250 HX | 11.93 | PEG 400 | 1.98 | malleable sponge |
| HEC 250 HHX | 4.77 | — | — | malleable sponge |
| HEC 250 HHX | 11.93 | — | — | malleable sponge |
| HEC 250 HHX | 4.77 | PEG 400 | 1.98 | malleable sponge |
| HEC 250 HHX | 11.93 | PEG 400 | 1.98 | malleable sponge |
| HEC 250 HHX | 11.93 | PEG 400 | 3.97 | malleable sponge |
| Carbomer | 3.77 | PEG 400 | 1.25 | powder |
| Carbomer | 1.47 | PEG 400 | 0.98 | powder |
| Carbomer | 1.93 | PEG 400 | 0.99 | powder |
| Carbomer | 1.79 | PEG 400 | 0.99 | powder |
| HPC GF | 19.09 | — | — | malleable sponge |
| HPC GF | 23.87 | — | — | malleable sponge |
| HPC GF | 19.09 | PEG 400 | 4.77 | no sponge texture |
| HPC GF | 23.87 | PEG 400 | 5.96 | film |
| HPC GF | 23.87 | PEG 400 | 7.95 | film |
| HPC LF | 7.95 | PEG 400 | 1.98 | sticky sponge |
| HPC LF | 11.93 | PEG 400 | 1.98 | sticky sponge |
| HPC HF | 1.98 | PEG 400 | 0.99 | sticky sponge |
| HPMC E5 | 7.95 | PEG 400 | 3.97 | malleable sponge |
| HPC GF | 1.98 | | | |
| HPMC E5 | 7.95 | PEG 400 | 3.97 | malleable sponge |
| HPC GF | 3.97 | | | |
| HPMC 4000 | 3.97 | PEG 400 | 3.97 | malleable sponge |
| HPC GF | 1.98 | | | |
| HPMC 4000 | 3.97 | PEG 400 | 3.97 | malleable sponge |
| HPC GF | 3.97 | | | |
| HPMC 4000 | 6.36 | PEG 400 | 3.97 | malleable sponge |
| HPC GF | 1.98 | | | |
| HPMC 4000 | 6.36 | PEG 400 | 3.97 | malleable sponge |
| HPC GF | 3.97 | | | |
| HPMC 4000 | 7.95 | PEG 400 | 3.97 | malleable sponge |
| HPC GF | 1.98 | | | |
| HPMC 4000 | 7.95 | PEG 400 | 3.97 | malleable sponge |
| HPC GF | 3.97 | | | |
| HPMC 4000 | 6.36 | PEG 4000 | 1.19 | malleable sponge |
| HPC GF | 1.98 | | | |
| HPMC 4000 | 7.95 | PEG 4000 | 1.19 | malleable sponge |
| HPC GF | 3.97 | | | |

It was found that compositions based on HPMC, HEC and NaCMC allowed for the formation of sponges with the desired characteristics, irrespective of the tested concentrations and the viscosity of the polymer. Compositions based on HPMC E5, HPMC E15, HPMC 4000, as well as HPMC K15, and compositions based on HEC H4000, HEC 250 M, HEC 250 HHX, as well as HEC 250 HX, allowed for the formation of sponges. Compositions based on HPC GF allowed for the formation of sponges with the desired characteristics when used in the absence of a plasticizer, while the presence of a plasticizer resulted in the formation of bioadhesive films or did not show a sponge-like texture. The compositions based on carbomer and HPC LF and HPC HF resulted, respectively, in powder or in sponges that were very sticky and not very malleable. Sponges with the desired characteristics were also obtained with compositions based on a combination of HPMC E5 and HPC GF and a combination of HPMC 4000 and HPC GF, all in the presence of plasticizer.

The sponges based on PEG seemed to be more resistant to rupture than the sponges based on PG. Both, PEG 400 and PEG 4000 may be used to obtain sponges with the desired characteristics, although higher concentrations of PEG 4000 often resulted in brittle sponges.

Residual amounts of water for the different types of polymers are listed in Table 2.

TABLE 2

| HPMC | 1.5-8 weight % |
|---|---|
| NaCMC | 5.5-14 weight % |
| HEC | 1-6 weight % |
| HPC | 3.5-7 weight % |
| Carbomer | not recoverable for residual water determination |

NaCMC-based sponges appear to retain more residual water than, for instance, HPMC-based sponges. It has been found that varying the amount of water for preparing the dispersion (4, 5 and 6 ml) did not influence the final residual amount of water after lyophilization.

For the evaluation of the speed of rehydration, discs of 1.2 cm diameter were rehydrated with 50 μl distilled water or the entire sponge ad 3 g with distilled water. Rehydration of the sponge resulted in the formation of a gel with varying viscosity. The speed of rehydration depended on the nature and the quantity of the polymer and, hence, can easily be modulated. For instance, it has been found that HEC 250HX- and 250M-based sponges allowed for a faster rehydration than HEC 250HHX- and H4000-based sponges. Irrespective of the polymer, the speed of rehydration diminished with an increasing concentration of polymer.

Example 4

Evaluation of Different Lyophilized Cidofovir-containing Compositions

Different conditions and concentrations of the components were tested to evaluate the desired characteristics of the lyophilisate. Desired characteristics are a sponge texture that is easily malleable when dry and that can be rapidly rehydrated into a gel with intermediate viscosity (i.e., not too liquid and not too viscous).

The lyophilization cycle was kept constant for ease of comparison, and in most conditions, the diameter of the crystallizer was 4 cm and the quantity of water added for the dispersion of the components was ad 6 g.

Tables 3 to 45 list the conditions and evaluation for each of the tested compositions. Indicated is the concentration in $mg/cm^2$ lyophilized sponge and the weight % in the aqueous composition before lyophilization of the type of polymer (HPMC, NaCMC, HEC, Carbomer or HPC) and the type of plasticizer (no plasticizer, PEG 400 or PG) and cidofovir. Additionally indicated is the amount of NaOH (provided as a 2 M stock solution), the diameter of the crystallizer, and, hence, the sponge after lyophilization (circular structure), the weight of the aqueous composition before lyophilization, the weight of the sponge after lyophilization, and the percentage of residual water in the sponge after lyophilization.

It can be seen that the addition of cidofovir to the composition modifies the properties of the sponge. Although placebo sponges with good quality could be obtained based on HPMC, HEC and NaCMC as a polymer, it appears that NaCMC-based sponges with cidofovir become very rigid and brittle (irrespective of concentrations and conditions). HPMC-based sponges are malleable and of good quality, although they have a slightly different appearance than their placebo counterparts and present very faint cracks when the sponge is folded in two. In contrast to their placebo counterparts, HEC 250HX-based sponges that contain cidofovir need a plasticizer to avoid rupture of the sponges (too brittle).

It appears that PG-based sponges are only slightly malleable and brittle, in contrast to PEG 400-based sponges, which are malleable and of good quality.

It has been found that irrespective of the tested polymer, the speed of rehydration decreases when the concentration of the polymer increases.

Tables 3 to 45 show some specific examples of compositions that present good-quality malleable sponges after lyophilization. Their rehydration capacities have also been tested in some cases. The conditions in which non-malleable sponges were obtained are also shown for comparison.

TABLE 3

| | | |
|---|---|---|
| HPMC E5 | $mg/cm^2$ | 7.95 |
| | % | 1.43 |
| Cidofovir | $mg/cm^2$ | 4.77 |
| | % | 0.86 |
| NaOH 2M ($mg/cm^2$) | | 12.33 |
| diameter lyophilisate (cm) | | 4 |
| weight before lyophilization (g) | | 7 |

TABLE 3-continued

| | |
|---|---|
| weight after lyophilization (mg) | 145.4 |
| residual water (%) | 7.74 |
| structure | malleable sponge |
| rehydration | nd |

TABLE 4

| | | |
|---|---|---|
| HPMC E5 | $mg/cm^2$ | 7.95 |
| | % | 1.67 |
| Cidofovir | $mg/cm^2$ | 4.77 |
| | % | 1 |
| NaOH 2M ($mg/cm^2$) | | 12.33 |
| diameter lyophilisate (cm) | | 4 |
| weight before lyophilization (g) | | 6 |
| weight after lyophilization (mg) | | 159.6 |
| residual water (%) | | 7.68 |
| structure | | malleable sponge |
| rehydration | | nd |

TABLE 5

| | | |
|---|---|---|
| HPMC E5 | $mg/cm^2$ | 3.97 |
| | % | 0.83 |
| Cidofovir | $mg/cm^2$ | 4.77 |
| | % | 1 |
| NaOH 2M ($mg/cm^2$) | | 12.33 |
| diameter lyophilisate (cm) | | 4 |
| weight before lyophilization (g) | | 6 |
| weight after lyophilization (mg) | | 115.17 |
| residual water (%) | | nd |
| structure | | malleable sponge |
| rehydration | | nd |

TABLE 6

| | | |
|---|---|---|
| HPMC E5 | $mg/cm^2$ | 2.45 |
| | % | 1 |
| Cidofovir | $mg/cm^2$ | 0.36 |
| | % | 0.15 |
| PEG 400 | $mg/cm^2$ | 0.49 |
| | % | 0.2 |
| NaOH 2M ($mg/cm^2$) | | 1.473 |
| diameter lyophilisate (cm) | | 7.2 |
| weight before lyophilization (g) | | 10 |
| weight after lyophilization (mg) | | 200 |
| residual water (%) | | 7.073 |
| structure | | malleable sponge |
| rehydration | | very rapid |

TABLE 7

| | | |
|---|---|---|
| HPMC E5 | $mg/cm^2$ | 3.14 |
| | % | 1 |
| Cidofovir | $mg/cm^2$ | 0.94 |
| | % | 0.30 |
| PEG 400 | $mg/cm^2$ | 0.63 |
| | % | 0.2 |
| NaOH 2M ($mg/cm^2$) | | 3.77 |
| diameter lyophilisate (cm) | | 4.5 |
| weight before lyophilization (g) | | 5 |
| weight after lyophilization (mg) | | 100 |
| residual water (%) | | 8.63 |
| structure | | malleable sponge |
| rehydration | | very rapid |

TABLE 8

| | | |
|---|---|---|
| HPMC E5 | $mg/cm^2$ | 3.97 |
| | % | 0.83 |
| Cidofovir | $mg/cm^2$ | 4.77 |
| | % | 1 |
| PEG 400 | $mg/cm^2$ | 1.98 |
| | % | 0.42 |

TABLE 8-continued

| | | |
|---|---|---|
| NaOH 2M (mg/cm$^2$) | | 12.33 |
| diameter lyophilisate (cm) | | 4 |
| weight before lyophilization (g) | | 6 |
| weight after lyophilization (mg) | | 128.67 |
| residual water (%) | | 6.0835 |
| structure | | malleable sponge |
| rehydration | | nd |

TABLE 9

| | | |
|---|---|---|
| HPMC E5 | mg/cm$^2$ | 6.36 |
| | % | 1.33 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 166.485 |
| residual water (%) | | nd |
| structure | | malleable sponge |
| rehydration | | nd |

TABLE 10

| | | |
|---|---|---|
| HPMC E5 | mg/cm$^2$ | 7.95 |
| | % | 1.43 |
| Cidofovir | mg/cm$^2$ | 4.77 |
| | % | 0.86 |
| PEG 400 | mg/cm$^2$ | 1.98 |
| | % | 0.36 |
| NaOH 2M (mg/cm$^2$) | | 12.33 |
| diameter lyophilisate (cm) | | 4 |
| weight before lyophilization (g) | | 7 |
| weight after lyophilization (mg) | | 166.6 |
| residual water (%) | | 7.084 |
| structure | | malleable sponge |
| rehydration | | nd |

TABLE 11

| | | |
|---|---|---|
| HPMC E5 | mg/cm$^2$ | 7.95 |
| | % | 1.67 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 183.695 |
| residual water (%) | | 7.51 |
| structure | | malleable sponge |
| rehydration | | nd |

TABLE 12

| | | |
|---|---|---|
| HPMC E5 | mg/cm$^2$ | 7.95 |
| | % | 1.67 |
| Cidofovir | mg/cm$^2$ | 2.38 |
| | % | 0.5 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 151.24 |
| residual water (%) | | 5.867 |
| structure | | malleable sponge |
| rehydration | | nd |

TABLE 13

| | | |
|---|---|---|
| HPMC E5 | mg/cm$^2$ | 11.93 |
| | % | 2.5 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 236.74 |
| residual water (%) | | nd |
| structure | | malleable sponge |
| rehydration | | nd |

TABLE 14

| | | |
|---|---|---|
| HPMC E5 | mg/cm$^2$ | 12.57 |
| | % | 1.67 |
| Cidofovir | mg/cm$^2$ | 1.88 |
| | % | 0.25 |
| PEG 400 | mg/cm$^2$ | 2.51 |
| | % | 0.33 |
| NaOH 2M (mg/cm$^2$) | | 3.77 |
| diameter lyophilisate (cm) | | 4.5 |
| weight before lyophilization (g) | | 12 |
| weight after lyophilization (mg) | | nd |
| residual water (%) | | nd |
| structure | | malleable sponge |
| rehydration | | nd |

TABLE 15

| | | |
|---|---|---|
| HPMC E5 | mg/cm$^2$ | 15.91 |
| | % | 3.33 |
| Cidofovir | mg/cm$^2$ | 2.387 |
| | % | 0.5 |
| PEG 400 | mg/cm$^2$ | 1.98 |
| | % | 0.42 |
| NaOH 2M (mg/cm$^2$) | | 6.127 |
| diameter lyophilisate (cm) | | 4 |
| weight before lyophilization (g) | | 6 |
| weight after lyophilization (mg) | | 246.91 |
| residual water (%) | | 4.6845 |
| structure | | malleable sponge |
| rehydration | | nd |

TABLE 16

| | | |
|---|---|---|
| HPMC E5 | mg/cm$^2$ | 3.97 |
| | % | 0.83 |
| Cidofovir | mg/cm$^2$ | 4.77 |
| | % | 1 |
| PEG 400 | mg/cm$^2$ | 3.97 |
| | % | 0.83 |
| NaOH 2M (mg/cm$^2$) | | 12.33 |
| diameter lyophilisate (cm) | | 4 |
| weight before lyophilization (g) | | 6 |
| weight after lyophilization (mg) | | 163.39 |
| residual water (%) | | 6.92 |
| structure | | malleable sponge |
| rehydration | | nd |

TABLE 17

| | | |
|---|---|---|
| HPMC E5 | mg/cm$^2$ | 6.366 |
| | % | 1.33 |
| Cidofovir | mg/cm$^2$ | 4.77 |
| | % | 1 |
| PEG 400 | mg/cm$^2$ | 3.97 |
| | % | 0.83 |
| NaOH 2M (mg/cm$^2$) | | 12.33 |

TABLE 17-continued

| | | |
|---|---|---|
| diameter lyophilisate (cm) | | 4 |
| weight before lyophilization (g) | | 6 |
| weight after lyophilization (mg) | | 186.82 |
| residual water (%) | | 4.935 |
| structure | | malleable sponge |
| rehydration | | nd |

TABLE 18

| | | |
|---|---|---|
| HPMC E5 | mg/cm$^2$ | 7.95 |
| | % | 1.67 |
| Cidofovir | mg/cm$^2$ | 4.77 |
| | % | 1 |
| PEG 400 | mg/cm$^2$ | 3.97 |
| | % | 0.83 |
| NaOH 2M (mg/cm$^2$) | | 12.33 |
| diameter lyophilisate (cm) | | 4 |
| weight before lyophilization (g) | | 6 |
| weight after lyophilization (mg) | | 208.64 |
| residual water (%) | | 5.2428 |
| structure | | malleable sponge |
| rehydration | | nd |

TABLE 19

| | | |
|---|---|---|
| HPMC E5 | mg/cm$^2$ | 7.95 |
| | % | 1.67 |
| Cidofovir | mg/cm$^2$ | 2.38 |
| | % | 0.50 |
| PEG 400 | mg/cm$^2$ | 3.97 |
| | % | 0.83 |
| NaOH 2M (mg/cm$^2$) | | 6.167 |
| diameter lyophilisate (cm) | | 4 |
| weight before lyophilization (g) | | 6 |
| weight after lyophilization (mg) | | 176.275 |
| residual water (%) | | nd |
| structure | | malleable sponge |
| rehydration | | nd |

TABLE 20

| | | |
|---|---|---|
| HPMC E5 | mg/cm$^2$ | 15.91 |
| | % | 3.33 |
| Cidofovir | mg/cm$^2$ | 4.77 |
| | % | 1 |
| PEG 400 | mg/cm$^2$ | 3.97 |
| | % | 0.83 |
| NaOH 2M (mg/cm$^2$) | | 12.33 |
| diameter lyophilisate (cm) | | 4 |
| weight before lyophilization (g) | | 6 |
| weight after lyophilization (mg) | | 304.663 |
| residual water (%) | | 5.6819 |
| structure | | malleable sponge |
| rehydration | | nd |

TABLE 21

| | | |
|---|---|---|
| HPMC E5 | mg/cm$^2$ | 7.95 |
| | % | 1.67 |
| Cidofovir | mg/cm$^2$ | 4.77 |
| | % | 1 |
| PG | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 168.675 |
| residual water (%) | | nd |
| structure | | slightly malleable sponge |
| rehydration | | nd |

TABLE 22

| | | |
|---|---|---|
| HPMC E5 | mg/cm$^2$ | 7.95 |
| | % | 1.67 |
| Cidofovir | mg/cm$^2$ | 2.38 |
| | % | 0.5 |
| PG | mg/cm$^2$ | 1.98 |
| | % | 0.42 |
| NaOH 2M (mg/cm$^2$) | | 6.167 |
| diameter lyophilisate (cm) | | 4 |
| weight before lyophilization (g) | | 6 |
| weight after lyophilization (mg) | | 139.05 |
| residual water (%) | | nd |
| structure | | slightly malleable and brittle sponge |
| rehydration | | nd |

TABLE 23

| | | |
|---|---|---|
| HPMC E5 | mg/cm$^2$ | 7.95 |
| | % | 1.67 |
| Cidofovir | mg/cm$^2$ | 4.77 |
| | % | 1 |
| PG | mg/cm$^2$ | 3.97 |
| | % | 0.83 |
| NaOH 2M (mg/cm$^2$) | | 12.33 |
| diameter lyophilisate (cm) | | 4 |
| weight before lyophilization (g) | | 6 |
| weight after lyophilization (mg) | | 184.79 |
| residual water (%) | | nd |
| structure | | slightly malleable and brittle sponge |
| rehydration | | nd |

TABLE 24

| | | |
|---|---|---|
| HPMC E15 | mg/cm$^2$ | 7.95 |
| | % | 1.67 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 197.145 |
| residual water (%) | | nd |
| structure | | malleable sponge |
| rehydration | | nd |

TABLE 25

| | | |
|---|---|---|
| HPMC 4000 | mg/cm$^2$ | 7.95 |
| | % | 1.67 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 196.65 |
| residual water (%) | | nd |
| structure | | malleable sponge |
| rehydration | | nd |

TABLE 26

| | | |
|---|---|---|
| HPMC 4000 | mg/cm$^2$ | 9.54 |
| | % | 2 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |

TABLE 26-continued

| | | |
|---|---|---|
| diameter lyophilisate (cm) | | 4 |
| weight before lyophilization (g) | | 6 |
| weight after lyophilization (mg) | | 193.39 |
| residual water (%) | | nd |
| structure | | malleable sponge |
| rehydration | | nd |

TABLE 27

| | | |
|---|---|---|
| HPMC 4000 | mg/cm² | 9.54 |
| | % | 2 |
| Cidofovir | mg/cm² | 4.77 |
| | % | 1 |
| PEG 400 | mg/cm² | 3.97 |
| | % | 0.83 |
| NaOH 2M (mg/cm²) | | 12.33 |
| diameter lyophilisate (cm) | | 4 |
| weight before lyophilization (g) | | 6 |
| weight after lyophilization (mg) | | 220.75 |
| residual water (%) | | 3.35 |
| structure | | malleable sponge |
| rehydration | | nd |

TABLE 28

| | | |
|---|---|---|
| HPMC 4000 | mg/cm² | 1.98 |
| | % | 0.42 |
| Cidofovir | mg/cm² | 2.38 |
| | % | 0.5 |
| PG | mg/cm² | 3.97 |
| | % | 0.83 |
| NaOH 2M (mg/cm²) | | 6.167 |
| diameter lyophilisate (cm) | | 4 |
| weight before lyophilization (g) | | 6 |
| weight after lyophilization (mg) | | 68.39 |
| residual water (%) | | nd |
| structure | | malleable sponge |
| rehydration | | nd |

TABLE 29

| | | |
|---|---|---|
| HPMC K15 | mg/cm² | 7.95 |
| | % | 1.67 |
| Cidofovir | mg/cm² | 4.77 |
| | % | 1 |
| PEG 400 | mg/cm² | 1.98 |
| | % | 0.42 |
| NaOH 2M (mg/cm²) | | 12.33 |
| diameter lyophilisate (cm) | | 4 |
| weight before lyophilization (g) | | 6 |
| weight after lyophilization (mg) | | 194.39 |
| residual water (%) | | nd |
| structure | | malleable sponge |
| rehydration | | nd |

TABLE 30

| | | |
|---|---|---|
| HPMC K15 | mg/cm² | 1.98 |
| | % | 0.42 |
| Cidofovir | mg/cm² | 2.38 |
| | % | 0.5 |
| PG | mg/cm² | 3.97 |
| | % | 0.83 |
| NaOH 2M (mg/cm²) | | 6.167 |
| diameter lyophilisate (cm) | | 4 |
| weight before lyophilization (g) | | 6 |
| weight after lyophilization (mg) | | 68.05 |
| residual water (%) | | nd |
| structure | | malleable sponge |
| rehydration | | nd |

TABLE 31

| | | |
|---|---|---|
| HEC 250M | mg/cm² | 7.95 |
| | % | 1.67 |
| Cidofovir | mg/cm² | 2.38 |
| | % | 0.5 |
| PEG 400 | mg/cm² | 1.98 |
| | % | 0.42 |
| NaOH 2M (mg/cm²) | | 6.167 |
| diameter lyophilisate (cm) | | 4 |
| weight before lyophilization (g) | | 6 |
| weight after lyophilization (mg) | | 144.34 |
| residual water (%) | | nd |
| structure | | malleable sponge |
| rehydration | | very rapid |

TABLE 32

| | | |
|---|---|---|
| HEC 250M | mg/cm² | 9.54 |
| | % | 2 |
| Cidofovir | mg/cm² | 4.77 |
| | % | 1 |
| PEG 400 | mg/cm² | 1.98 |
| | % | 0.42 |
| NaOH 2M (mg/cm²) | | 12.33 |
| diameter lyophilisate (cm) | | 4 |
| weight before lyophilization (g) | | 6 |
| weight after lyophilization (mg) | | 200.56 |
| residual water (%) | | 4.208 |
| structure | | malleable sponge |
| rehydration | | very rapid |

TABLE 33

| | | |
|---|---|---|
| HEC 250M | mg/cm² | 9.54 |
| | % | 2 |
| Cidofovir | mg/cm² | 4.77 |
| | % | 1 |
| PEG 400 | mg/cm² | 3.58 |
| | % | 0.75 |
| NaOH 2M (mg/cm²) | | 12.33 |
| diameter lyophilisate (cm) | | 4 |
| weight before lyophilization (g) | | 6 |
| weight after lyophilization (mg) | | 221.69 |
| residual water (%) | | nd |
| structure | | malleable sponge |
| rehydration | | nd |

TABLE 34

| | | |
|---|---|---|
| HEC 250 HX | mg/cm² | 7.95 |
| | % | 1.67 |
| Cidofovir | mg/cm² | 4.77 |
| | % | 1 |
| PEG 400 | mg/cm² | 1.98 |
| | % | 0.42 |
| NaOH 2M (mg/cm²) | | 12.33 |
| diameter lyophilisate (cm) | | 4 |
| weight before lyophilization (g) | | 6 |
| weight after lyophilization (mg) | | 183.155 |
| residual water (%) | | 3.44 |
| structure | | malleable sponge |
| rehydration | | rehydration immediate |

TABLE 35

| | | |
|---|---|---|
| HEC 250 HX | mg/cm² | 7.95 |
| | % | 1.67 |
| Cidofovir | mg/cm² | 4.77 |
| | % | 1 |
| PEG 400 | mg/cm² | — |
| | % | — |
| NaOH 2M (mg/cm²) | | 12.33 |

TABLE 35-continued

| | | |
|---|---|---|
| diameter lyophilisate (cm) | | 4 |
| weight before lyophilization (g) | | 6 |
| weight after lyophilization (mg) | | 149.95 |
| residual water (%) | | nd |
| structure | | brittle sponge |
| rehydration | | nd |

TABLE 36

| | | |
|---|---|---|
| NaCMC | mg/cm$^2$ | 4.77 |
| | % | 0.86 |
| Cidofovir | mg/cm$^2$ | 4.77 |
| | % | 0.86 |
| NaOH 2M (mg/cm$^2$) | | 12.33 |
| diameter lyophilisate (cm) | | 4 |
| weight before lyophilization (g) | | 7 |
| weight after lyophilization (mg) | | 113.4 |
| residual water (%) | | 8.265 |
| structure | | rigid and brittle sponge |
| rehydration | | nd |

TABLE 37

| | | |
|---|---|---|
| NaCMC | mg/cm$^2$ | 4.77 |
| | % | 1 |
| Cidofovir | mg/cm$^2$ | 4.77 |
| | % | 1 |
| NaOH 2M (mg/cm$^2$) | | 12.33 |
| diameter lyophilisate (cm) | | 4 |
| weight before lyophilization (g) | | 6 |
| weight after lyophilization (mg) | | 113.4 |
| residual water (%) | | 13.659 |
| structure | | very rigid and brittle sponge |
| rehydration | | nd |

TABLE 38

| | | |
|---|---|---|
| NaCMC | mg/cm$^2$ | 3.18 |
| | % | 0.67 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 157.335 |
| residual water (%) | | 8.635 |
| structure | | rigid and brittle sponge |
| rehydration | | nd |

TABLE 39

| | | |
|---|---|---|
| NaCMC | mg/cm$^2$ | 4.77 |
| | % | 0.86 |
| Cidofovir | mg/cm$^2$ | 4.77 |
| | % | 0.86 |
| PEG 400 | mg/cm$^2$ | 1.98 |
| | % | 0.36 |
| NaOH 2M (mg/cm$^2$) | | 12.33 |
| diameter lyophilisate (cm) | | 4 |
| weight before lyophilization (g) | | 7 |
| weight after lyophilization (mg) | | 133.25 |
| residual water (%) | | 10.631 |
| structure | | rigid and brittle sponge |
| rehydration | | nd |

TABLE 40

| | | |
|---|---|---|
| NaCMC | mg/cm$^2$ | 4.77 |
| | % | 1 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 146.65 |
| residual water (%) | | 6.51 |
| structure | | rigid and brittle sponge |
| rehydration | | nd |

TABLE 41

| | | |
|---|---|---|
| NaCMC | mg/cm$^2$ | 6.36 |
| | % | 1.33 |
| Cidofovir | mg/cm$^2$ | 4.77 |
| | % | 1 |
| PEG 400 | mg/cm$^2$ | 1.98 |
| | % | 0.42 |
| NaOH 2M (mg/cm$^2$) | | 12.33 |
| diameter lyophilisate (cm) | | 4 |
| weight before lyophilization (g) | | 6 |
| weight after lyophilization (mg) | | 149.65 |
| residual water (%) | | 11.964 |
| structure | | very rigid and brittle sponge |
| rehydration | | nd |

TABLE 42

| | | |
|---|---|---|
| NaCMC | mg/cm$^2$ | 4.77 |
| | % | 1 |
| Cidofovir | mg/cm$^2$ | 4.77 |
| | % | 1 |
| PEG 400 | mg/cm$^2$ | 3.97 |
| | % | 0.83 |
| NaOH 2M (mg/cm$^2$) | | 12.33 |
| diameter lyophilisate (cm) | | 4 |
| weight before lyophilization (g) | | 6 |
| weight after lyophilization (mg) | | 169.05 |
| residual water (%) | | 6.02 |
| structure | | very rigid and brittle sponge |
| rehydration | | nd |

TABLE 43

| | | |
|---|---|---|
| NaCMC | mg/cm$^2$ | 3.18 |
| | % | 0.67 |
| Cidofovir | mg/cm$^2$ | 2.38 |
| | % | 0.5 |
| PG | mg/cm$^2$ | 3.97 |
| | % | 0.83 |
| NaOH 2M (mg/cm$^2$) | | 6.167 |
| diameter lyophilisate (cm) | | 4 |
| weight before lyophilization (g) | | 6 |
| weight after lyophilization (mg) | | 90.42 |
| residual water (%) | | nd |
| structure | | slightly rigid and brittle sponge |
| rehydration | | nd |

TABLE 44

| | | |
|---|---|---|
| NaCMC | mg/cm$^2$ | 4.77 |
| | % | 1 |
| Cidofovir | mg/cm$^2$ | 4.77 |
| | % | 1 |
| PG | mg/cm$^2$ | 3.97 |
| | % | 0.83 |
| NaOH 2M (mg/cm$^2$) | | 12.33 |

TABLE 44-continued

| | | |
|---|---|---|
| diameter lyophilisate (cm) | | 4 |
| weight before lyophilization (g) | | 6 |
| weight after lyophilization (mg) | | 145.77 |
| residual water (%) | | nd |
| structure | | very rigid and brittle sponge |
| rehydration | | nd |

TABLE 45

| | | |
|---|---|---|
| NaCMC | mg/cm² | 4.77 |
| | % | 1 |
| Cidofovir | mg/cm² | 2.38 |
| | % | 0.5 |
| PG | mg/cm² | 3.97 |
| | % | 0.83 |
| NaOH 2M (mg/cm²) | | 6.167 |
| diameter lyophilisate (cm) | | 4 |
| weight before lyophilization (g) | | 6 |
| weight after lyophilization (mg) | | 108.08 |
| residual water (%) | | nd |
| structure | | very rigid and brittle sponge |
| rehydration | | nd |

After rehydration, a gel-like composition can be obtained. A preferred gel-like composition typically comprises about 2% cidofovir and 4% HEC250M. The composition typically comprises HCL and NaOH in a quantity to reach a pH value of 7.2. The remaining component of the gel-like composition is water, to reach 100%. If required, an antibacterial agent could be added to further improve the shelf-life. One example is Benzyl alcohol (about 2%).

Example 5

Water Content in the Sponge

The residual water in the sponge after lyophilization was measured by the Karl Fisher method (Metler DL35). From Table 46 it can be seen that the percentage residual water varies in function of the polymer as well as in function of the presence of cidofovir.

TABLE 46

| | PEG 400 | PG | Cidofovir | % water | n |
|---|---|---|---|---|---|
| HPMC E5 | | | | | |
| | 7.95 | 1.98 | | 3.08 ± 1.36 | 3 |
| | 6.36 | 3.97 | | 1.95 | 1 |
| | 7.95 | 3.97 | | 1.83 | 1 |
| | 15.91 | 3.97 | | 3.18 ± 1.94 | 5 |
| | 31.83 | 3.97 | | 1.89 ± 0.401 | 3 |
| | 7.95 | | 4.77 | 7.68 ± 1.34 | 3 |
| | 3.97 | 1.98 | 4.77 | 6.09 ± 0.35 | 2 |
| | 7.95 | 1.98 | 2.38 | 5.87 | 1 |
| | 7.95 | 1.98 | 4.77 | 7.39 ± 1.44 | 7 |
| | 15.91 | 1.98 | 2.38 | 4.68 | 1 |
| | 15.91 | 1.98 | 4.77 | 5.80 ± 1.08 | 2 |
| | 3.97 | 3.97 | 4.77 | 6.91 ± 1.71 | 3 |
| | 6.36 | 3.97 | 4.77 | 4.94 ± 0.5 | 2 |
| | 7.95 | 3.97 | 4.77 | 5.25 ± 1.12 | 3 |
| | 15.91 | 3.97 | 4.77 | 5.18 ± 0.67 | 4 |
| | 7.95 | | 1.98 | 2.69 | 1 |
| | 10.58 | | 2.63 | 3.33 | 1 |
| | 11.93 | | 2.94 | 3.18 ± 0.40 | 2 |
| | 7.95 | 3.97 | | 2.76 | 1 |
| | 15.91 | 3.97 | | 5.12 | 1 |
| HEC 250 HX | | | | | |
| | 7.95 | 1.98 | | 4.80 ± 1.4 | 15 |
| | 7.95 | 1.98 | 4.77 | 3.44 ± 0.33 | 3 |

TABLE 46-continued

| | PEG 400 | PG | Cidofovir | % water | n |
|---|---|---|---|---|---|
| HEC 250 M | | | | | |
| | 9.54 | 1.98 | | 4.44 ± 0.69 | 5 |
| | 9.54 | 1.98 | 4.77 | 4.21 ± 1.26 | 4 |
| HPMC 4000 | | | | | |
| | 9.54 | 1.98 | | 1.03 ± 0.06 | 3 |
| | 9.54 | 3.97 | 4.77 | 3.35 ± 0.01 | 2 |
| NaCMC | | | | | |
| | 4.77 | 1.98 | | 9.34 ± 1.98 | 3 |
| | 5.57 | 1.98 | | 8.19 | 1 |
| | 4.77 | 3.97 | | 6.86 | 1 |
| | 4.77 | | 4.77 | 11.86 ± 3.18 | 1 |
| | 3.18 | 1.98 | 4.77 | 8.64 ± 0.02 | 2 |
| | 4.77 | 1.98 | 4.77 | 6.51 | 1 |
| | 6.36 | 1.98 | 4.77 | 11.96 | 1 |
| | 4.77 | 3.97 | 4.77 | 6.02 | 1 |
| | 4.77 | | 1.98 | 8.33 | 1 |

The residual water content is lower in HPMC- and HEC-based sponges than in NaCMC-based sponges.

It has been established that the quantity of water that was added to obtain the aqueous composition before lyophilization (4, 5 or 6 ml were tested) did not influence the amount of residual water after lyophilization.

Example 6

Uniformity of Cidofovir

The uniformity of cidofovir presence inside the sponges has been tested by cutting sponges in four parts and testing the cidofovir dose by chromatography (HPLC). The conditions are as follows:
stationary phase: LiChrospher® 100 RP-18 e (endcapped) (5 µm) in an analytical LiChrocart® column of 250 mm×4 mm, d.i.
mobile phase: HPLC buffer pH 6.5/ACN (90/10, m/m)
flow rate: 1 ml/minute
temperature: 30° C.
detection: spectrophotometric adsorption, UV 275 nm
injection volume: 20 µl
The composition of the HPLC buffer is:
5 mM tetrabutyl ammonium hydrogen sulphate
5 mM ammonium dihydrogen phosphate
pH adjusted to 6.5 with ammonium
Table 47 lists the results for HPMC E5-based sponges, as a percentage of the theoretically expected dose.

TABLE 47

| lot No | location | % of theoretical |
|---|---|---|
| 10C24-3 | side | 95.67 |
| 10C24-3 | side | 112.77 |
| 10C24-3 | side | 87.86 |
| 10C24-3 | center | 92.39 |
| 10C24-4 | side | 101.03 |
| 10C24-4 | side | 100.57 |
| 10C24-4 | side | 95.24 |
| 10C24-4 | center | 95.83 |

Example 7

Stability of Cidofovir

Figure 1:
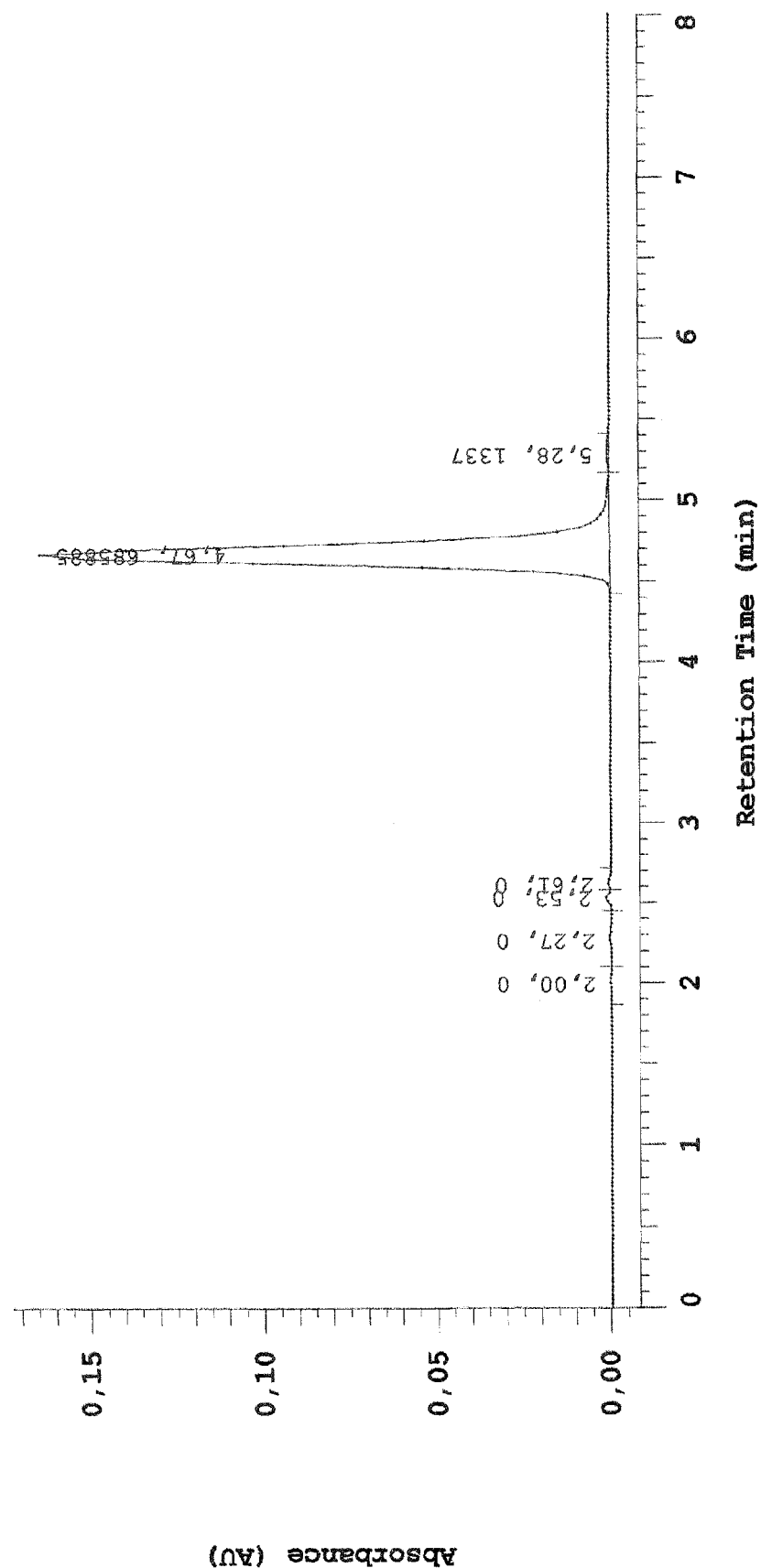
Figure 1:
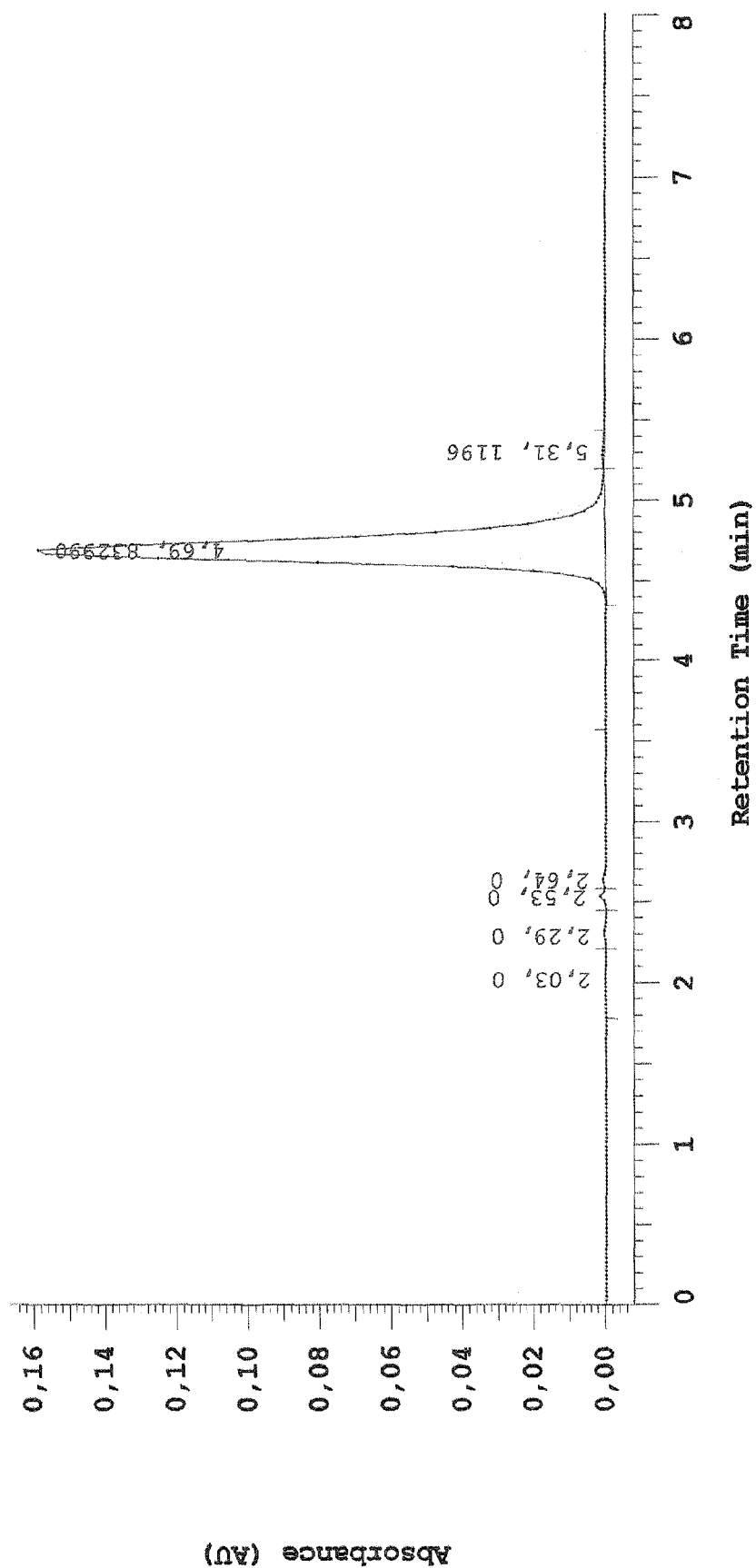
Figure 1:
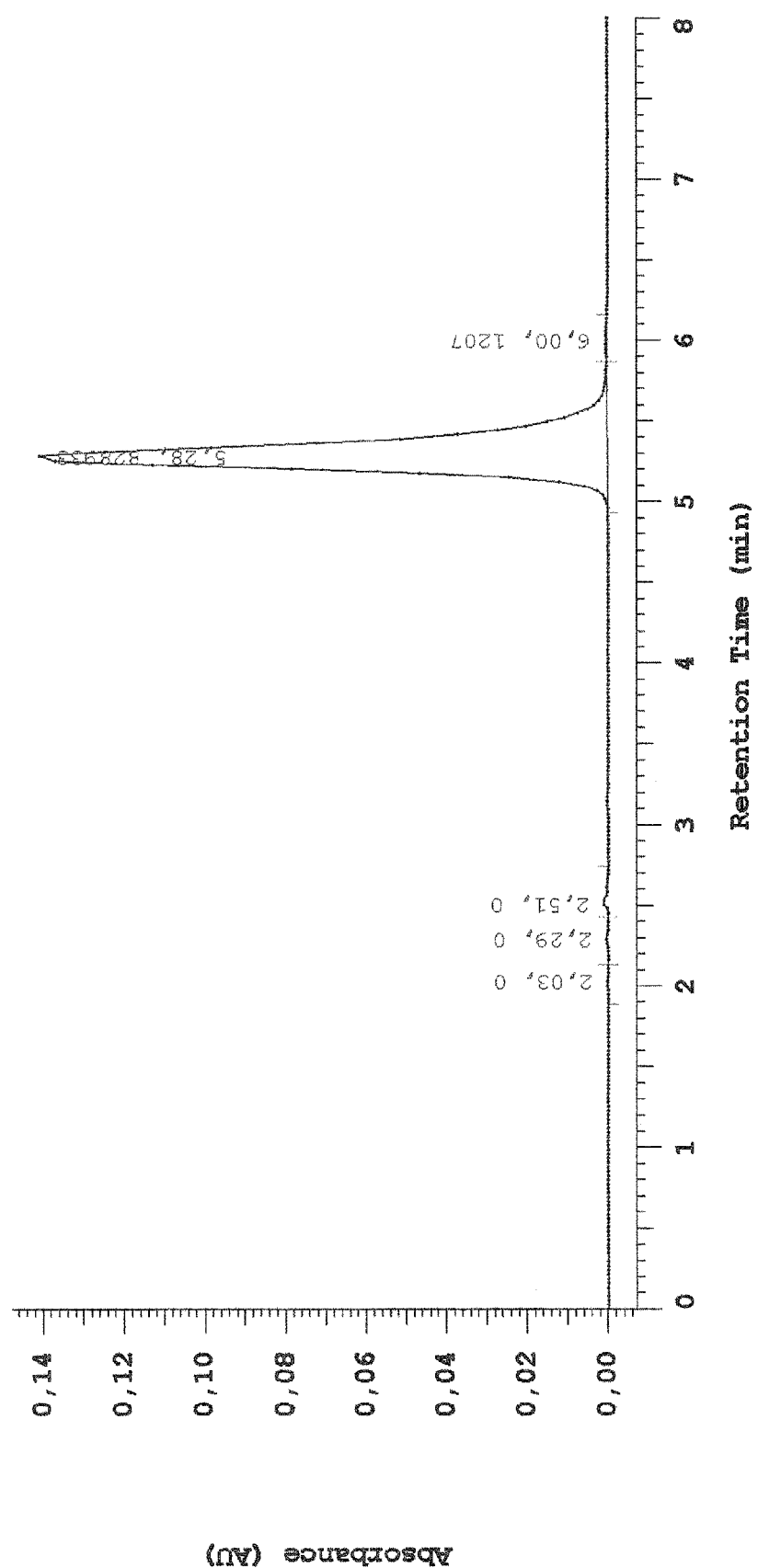
Figure 1:
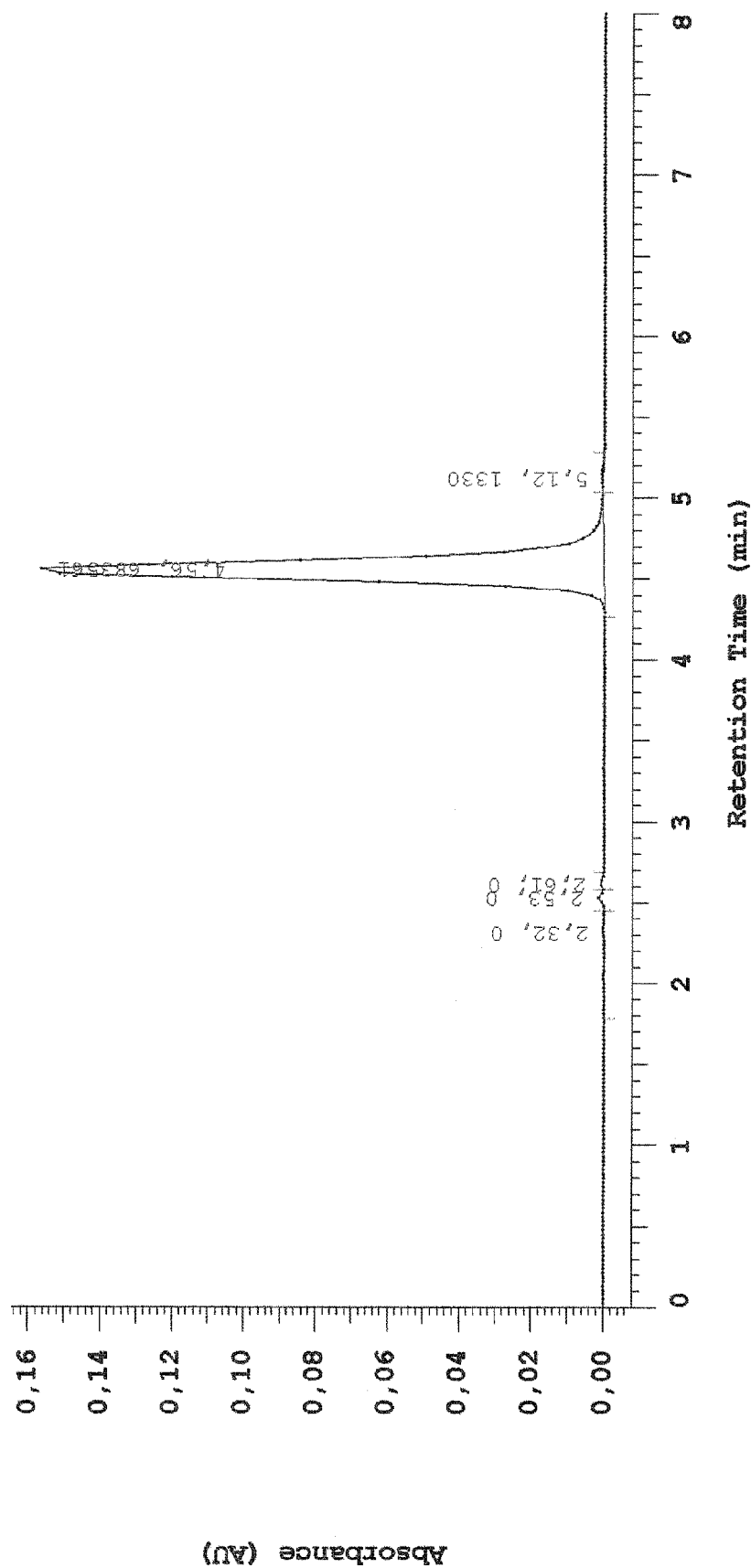
Figure 1:
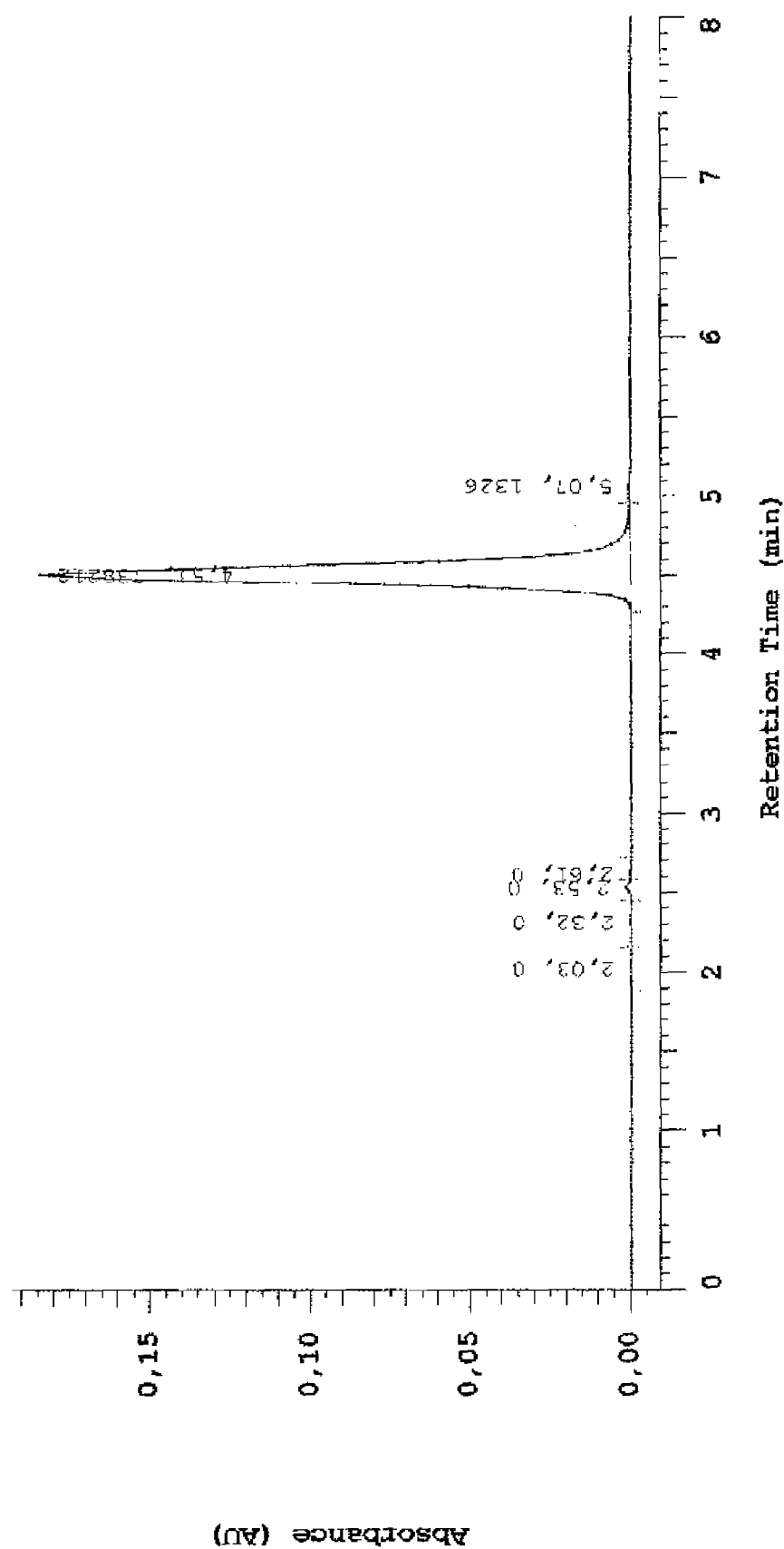
Figure 1:
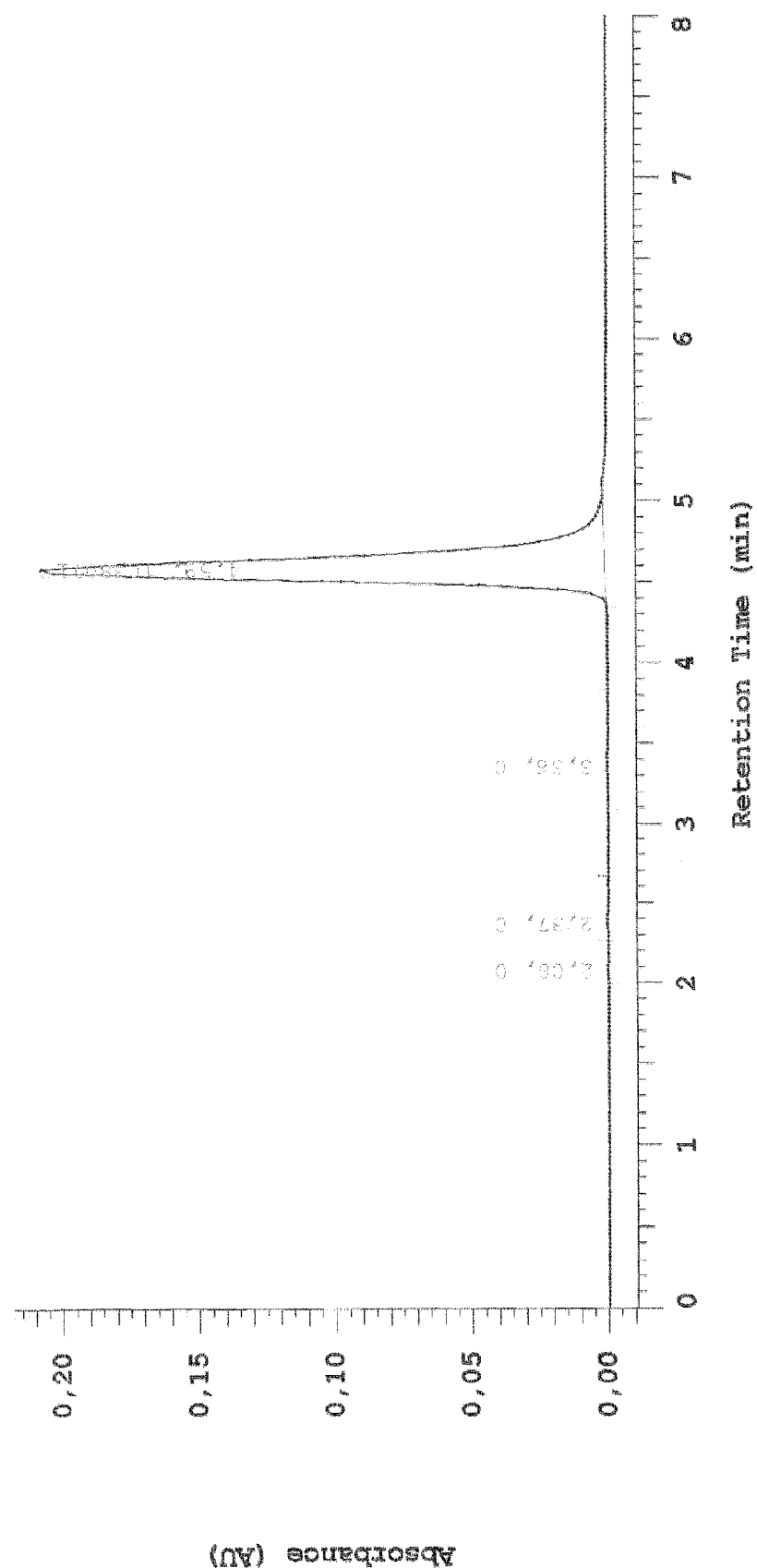
Figure 2:
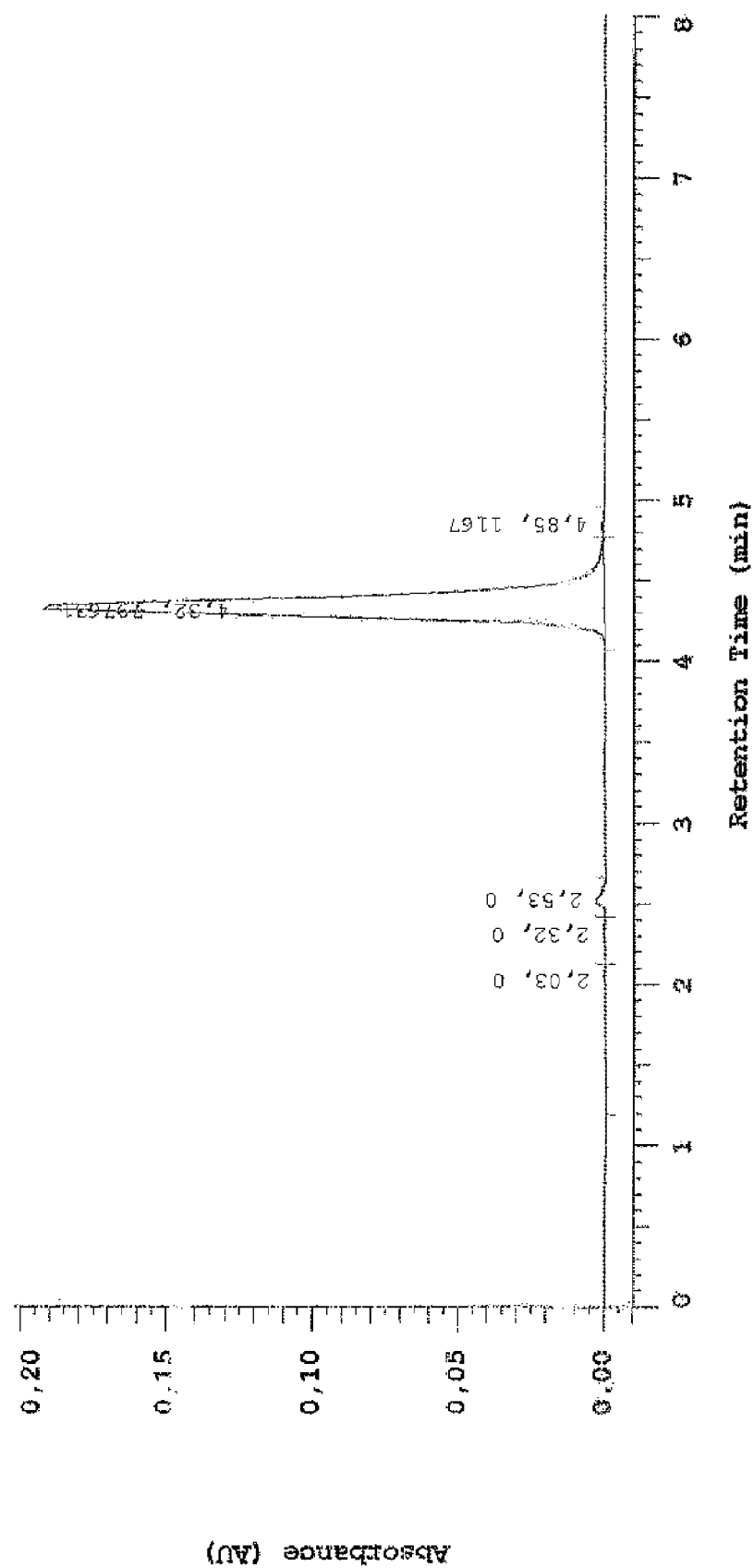
FIGS. 2A-2C: HPLC chromatograms of cidofovir showing absorbance (AU) in function of retention time (minutes).
Figure 2:
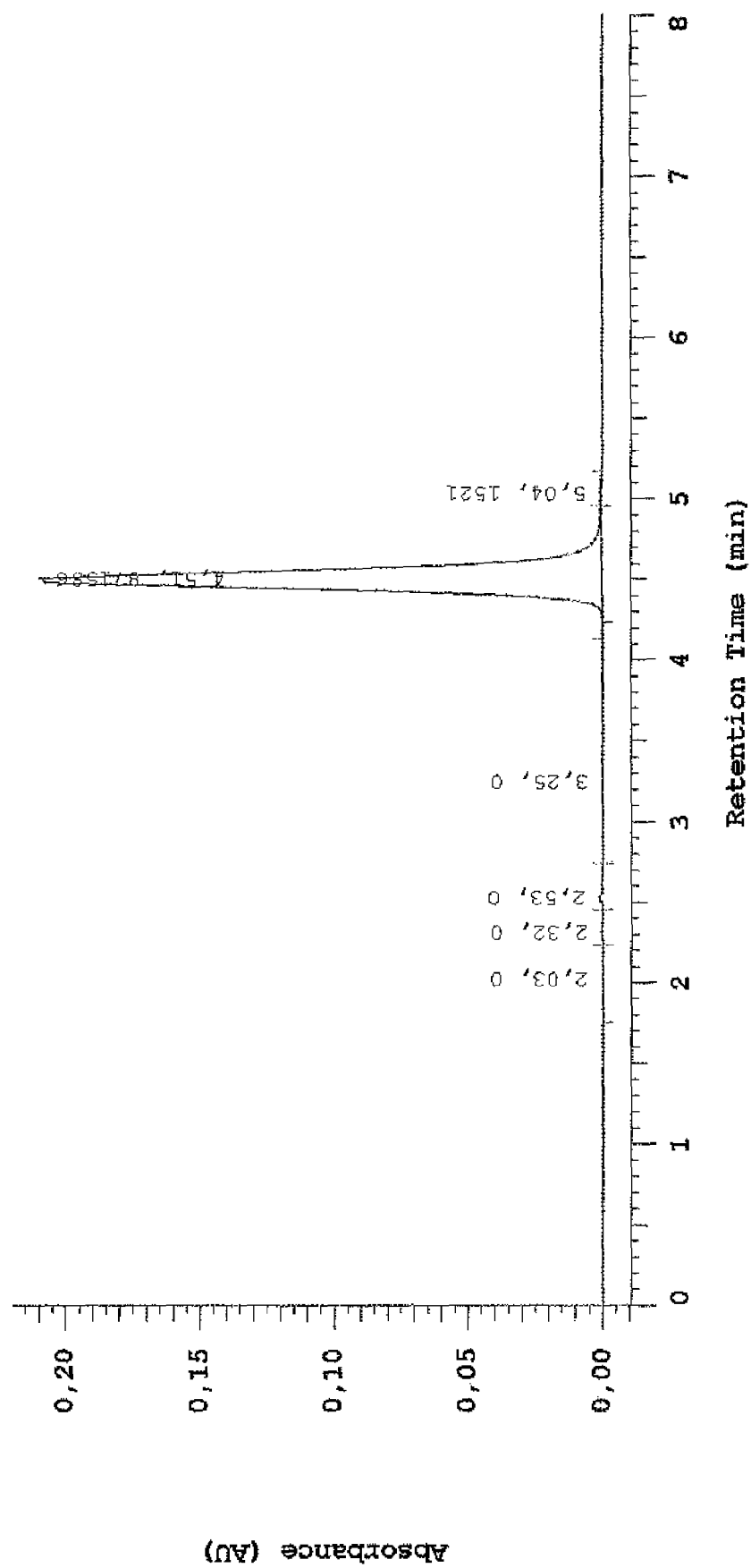

Lyophilized sponges have been bagged (PET/Al/EZ) and shielded from humidity, light and oxygen. The sponges were kept at three different temperatures: 4° C., 25° C. and 45° C. FIG. 1 shows the chromatograms of sponges that contained HPMC E5 (7.95 mg/cm$^2$), PEG 400 (1.98 mg/cm$^2$) and cidofovir (4.77 mg/cm$^2$). FIGS. 1A, 1B, 1C, 1D, 1E, 1F and 1G represent, respectively, the chromatograms of the calibration (100 µg/ml), the sponge at T0 and the sponge at T1, T3, T6, T9 and T12 (i.e., respectively, after one, three, six, nine and twelve month(s)) at 45° C. FIGS. 2A, 2B and 2C represent the chromatograms of a sponge comprising HEC 250HX (7.95 mg/cm$^2$), PEG 400 (1.98 mg/cm$^2$) and cidofovir (4.77 mg/cm$^2$), respectively, at T0, T1 and T3 (i.e., after one and three month(s)) at 45° C. It can be seen that the peak area is small (irrespective of the temperature at which the sponges are kept) and that the peak is equally present in the calibration chromatogram. Hence, the sponges are stable under the conditions tested.

Example 8

Diffusion of Cidofovir

Figure 3:
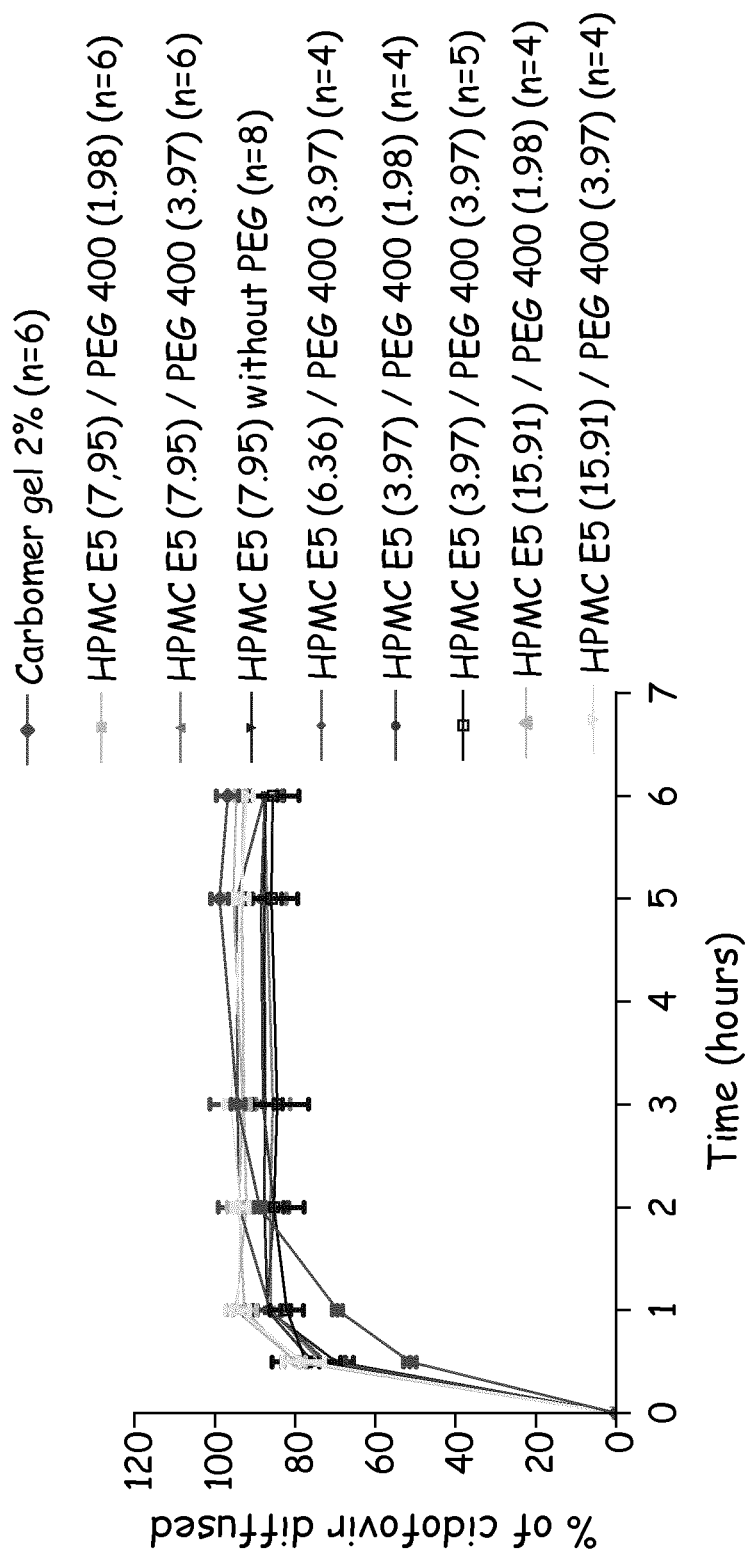
FIGS. 3A-3C: Diffusion kinetics of cidofovir, as measured with a Franz diffusion cell, showing the percentage (%) of diffused cidofovir in function of time (hours).
Figure 3:
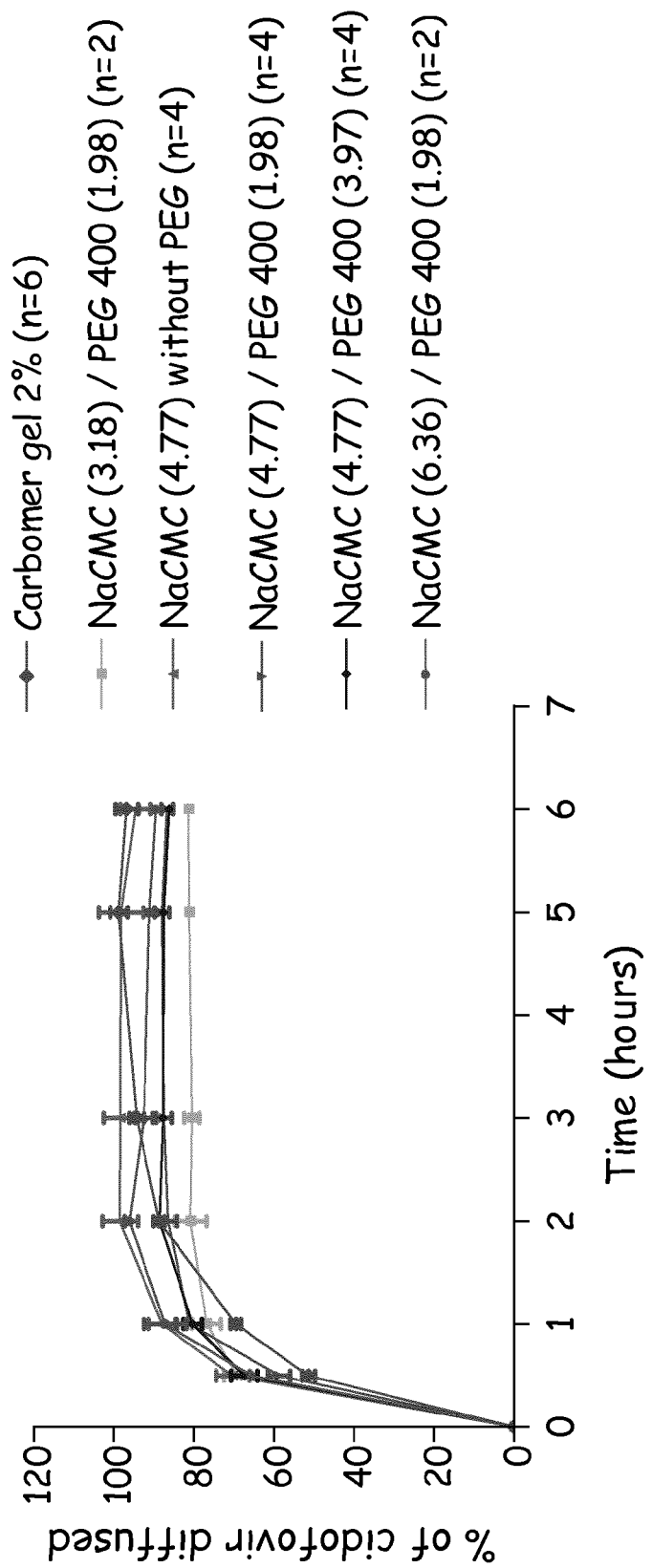
Figure 3:
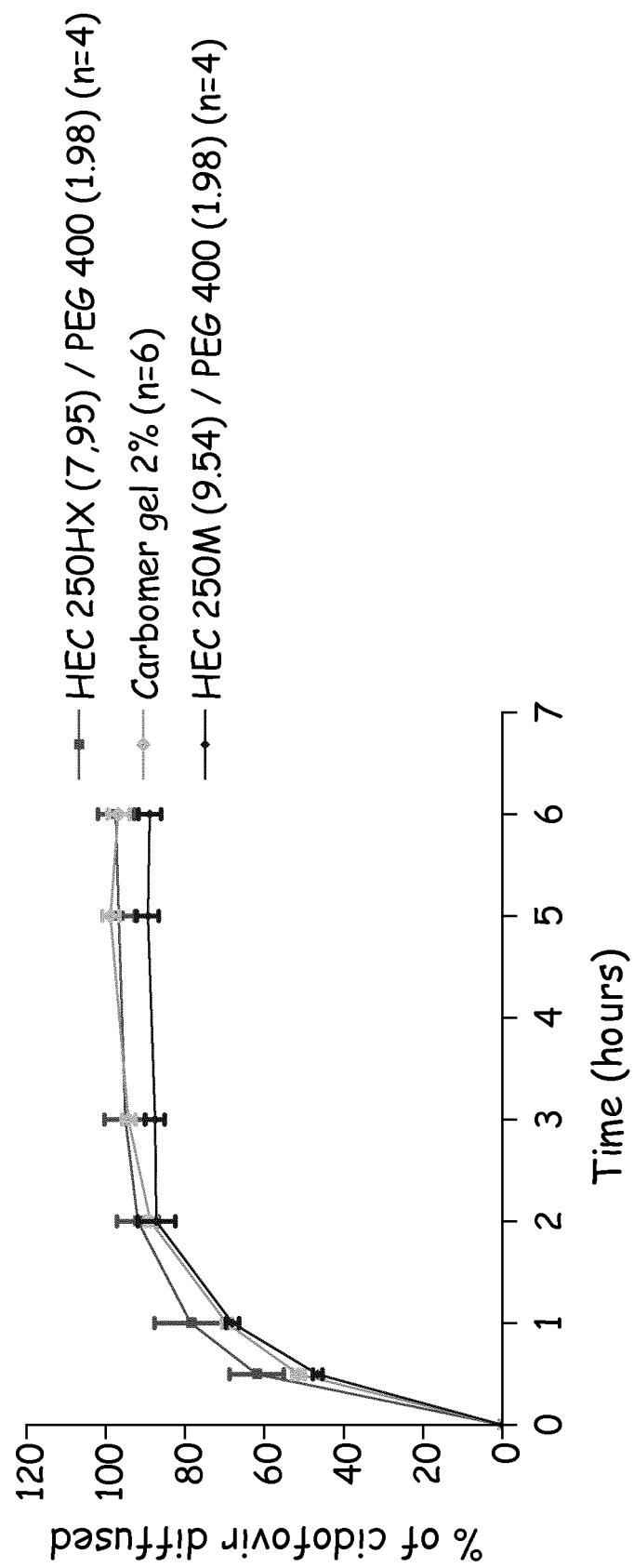
Figure 4:
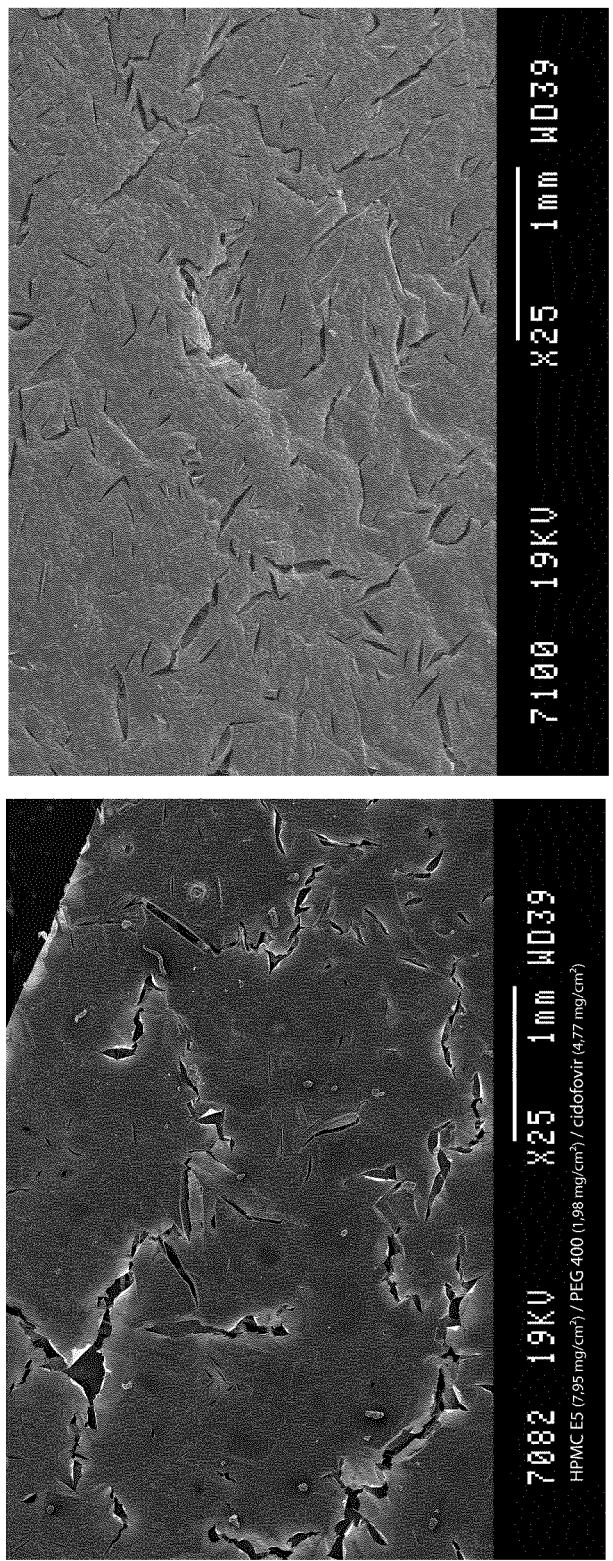
FIG. 4: Scanning electron microscopy (SEM) at 25× magnification of the external layer of compositions comprising HPMC E5 according to an embodiment of the disclosure. (left image) SEM of a composition according to an embodiment of the disclosure comprising PEG 400 as a plasticizer; and (right image) SEM of a composition according to an embodiment of the disclosure comprising PG as a plasticizer.
Figure 5:
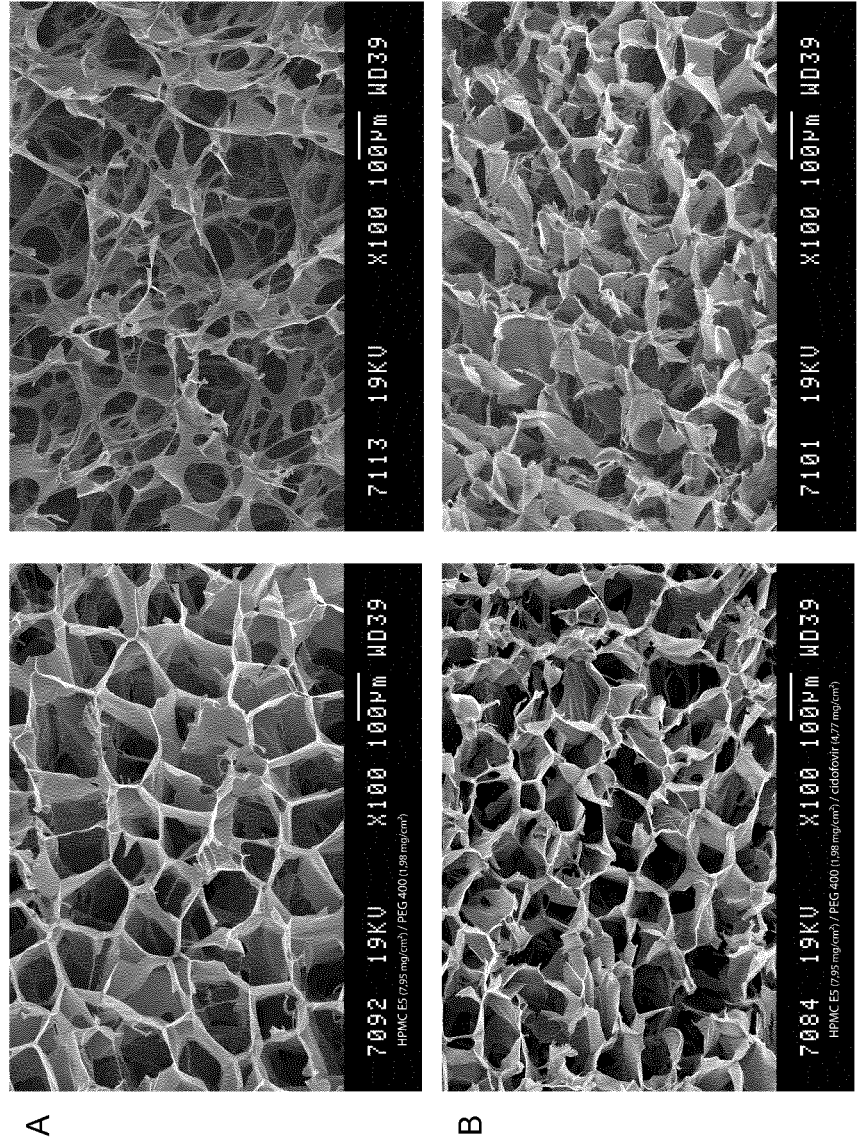
FIG. 5: Scanning electron microscopy (SEM) at 100× magnification of compositions comprising HPMC E5. (Row A) SEM of a placebo composition comprising PEG 400 (left image) or PG (right image) as a plasticizer; and (Row B) SEM of a composition according to an embodiment of the disclosure comprising PEG 400 (left image) or PG (right image) as a plasticizer.
Figure 6:
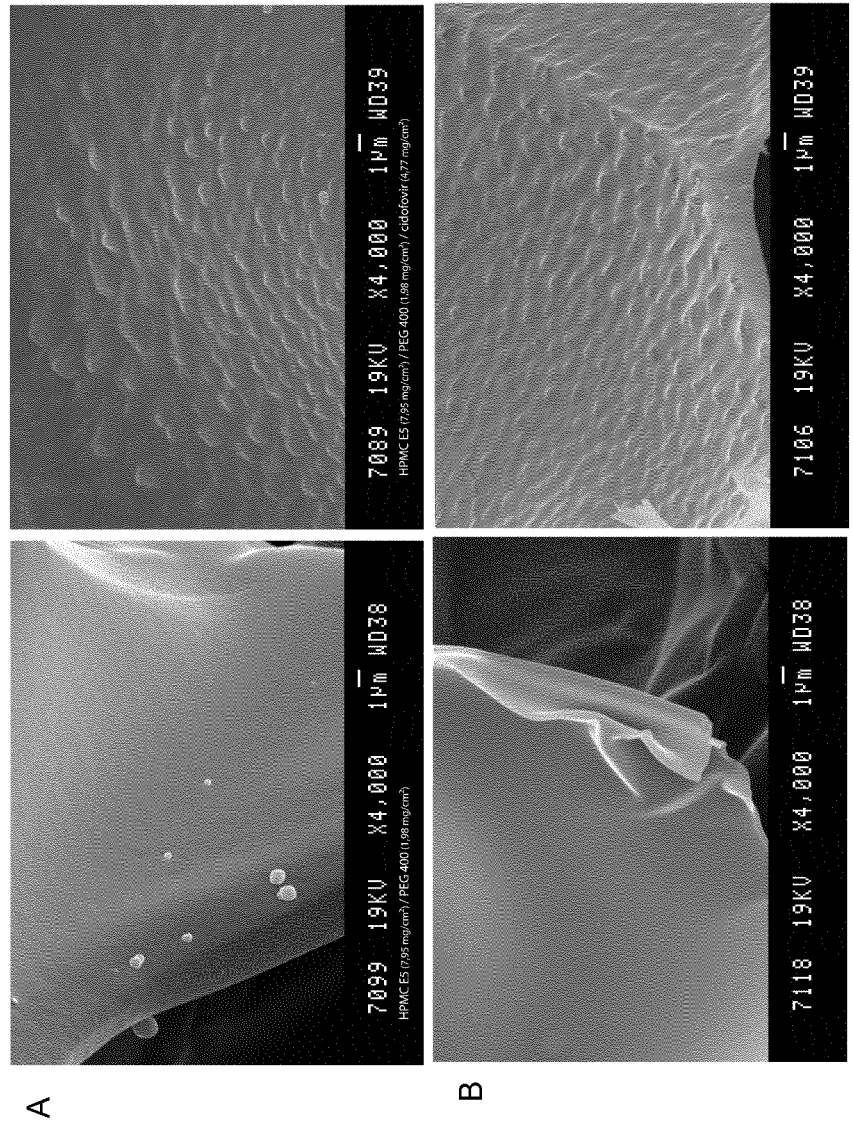
FIG. 6: Scanning electron microscopy (SEM) at 4000× magnification of compositions comprising HPMC E5. (Row A) SEM of a placebo composition (left image) or a composition according to an embodiment of the disclosure (right image), each comprising PEG 400 as a plasticizer; and (Row B) SEM of a placebo composition (left image) or a composition according to an embodiment of the disclosure (right image), each comprising PG as a plasticizer.
Figure 7:
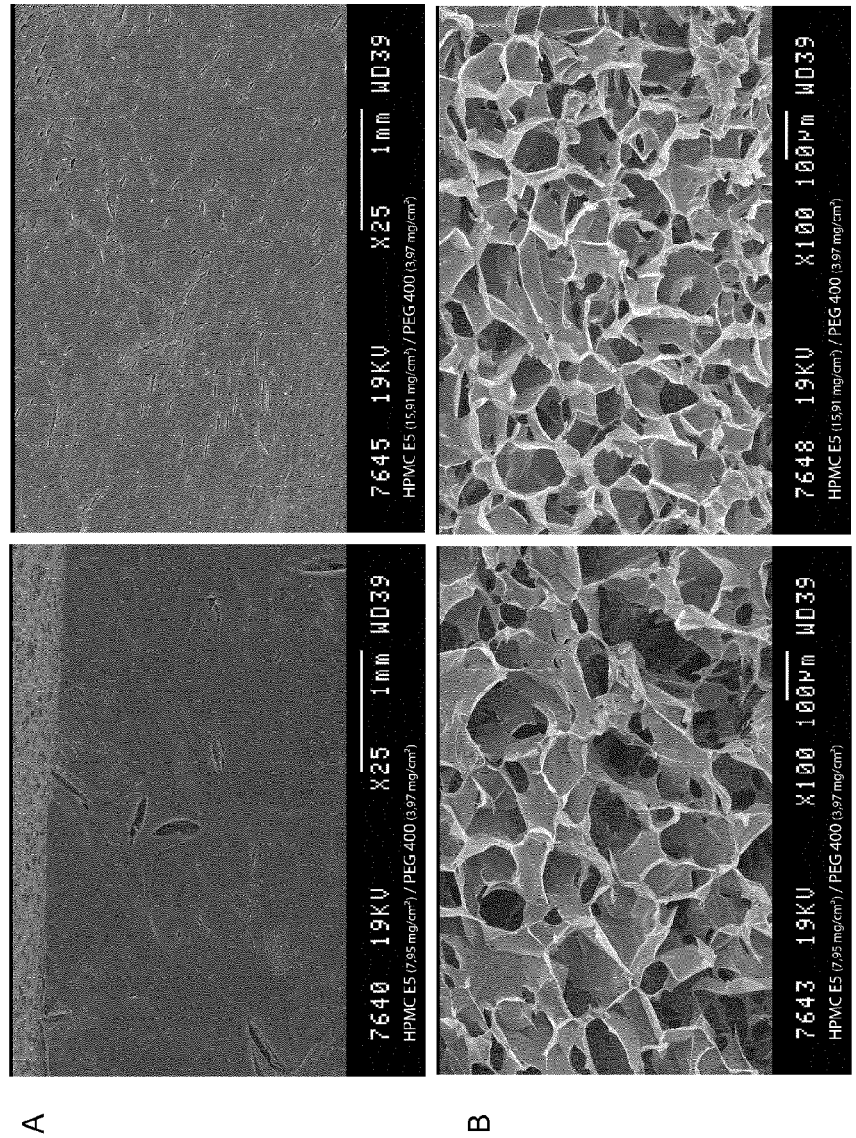
FIG. 7: Scanning electron microscopy (SEM) of placebo compositions comprising HPMC E5 as polymer and PEG 400 as plasticizer. (Row A) SEM at 25× magnification of the external layer of a composition comprising 7.95 mg/cm² (left image) or 15.91 mg/cm² (right image) of polymer. (Row B) SEM at 100× magnification of a composition comprising 7.95 mg/cm² (left image) or 15.91 mg/cm² (right image) of polymer.
Figure 8:
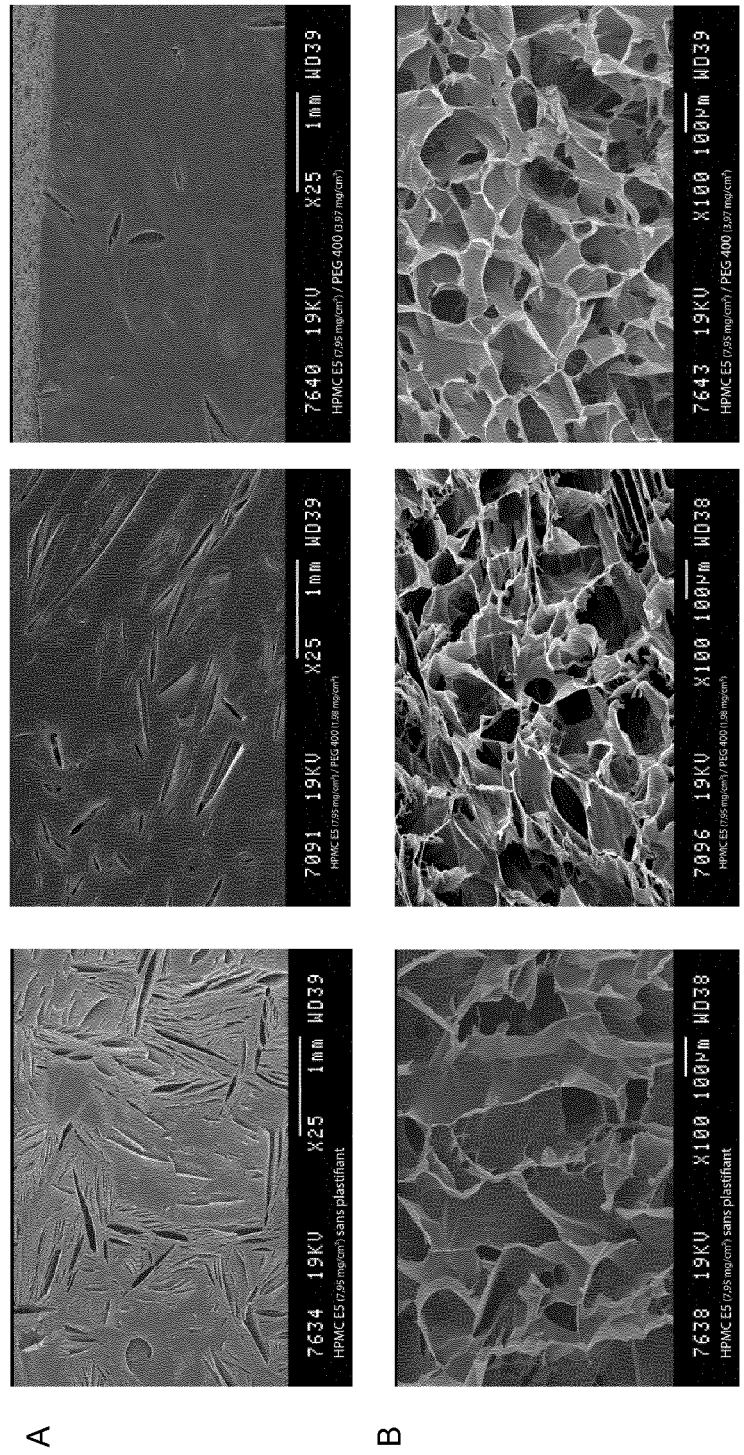
FIG. 8: Scanning electron microscopy (SEM) of placebo compositions comprising HPMC E5. (Row A) SEM at 25× magnification of the external layer of a composition comprising 0 mg/cm² (left image) or 1.98 mg/cm² (middle image) or 3.97 mg/cm² (right image) of PEG 400 as plasticizer. (Row B) SEM at 100× magnification of a composition comprising 0 mg/cm² (left image) or 1.98 mg/cm² (middle image) or 3.97 mg/cm² (right image) of PEG 400 as plasticizer.

Diffusion of cidofovir was measured with a Franz diffusion cell. A lyophilisate of 1.2 cm diameter was placed in the cell and rehydrated with 350 µl of a phosphate buffer (pH 5, 37° C.). The diffusion kinetics are evaluated by HPLC in doses of 1 ml. Polymers were varied (HPMC E5, NaCMC, HEC 250HX and HEC 250M) as well as the presence or absence of plasticizer (PEG 400). The concentration of cidofovir was kept constant. From FIGS. 3A, 3B and 3C, it seems that a plateau is reached for HPMC-based sponges after 1 hour, for NaCMC- and HEC 250M-based sponges after 2 hours, and for HEC 250HX-based sponges after 3 hours. Nevertheless, cidofovir diffuses fast from irrespective compositions.

Example 9

Microscopic Analysis

The structure of the sponges based on HPMC E5, HPMC 4000, HPMC K15 and HEC 250HX was evaluated by scanning electron microscopy. Pore structure was compared between sponges with different types of polymer, sponges with different concentrations of the polymer, sponges with or without cidofovir, sponges with or without plasticizer, as well as sponges with different plasticizers (PEG 400 or PG) and different concentrations of plasticizer.

Figure 9:
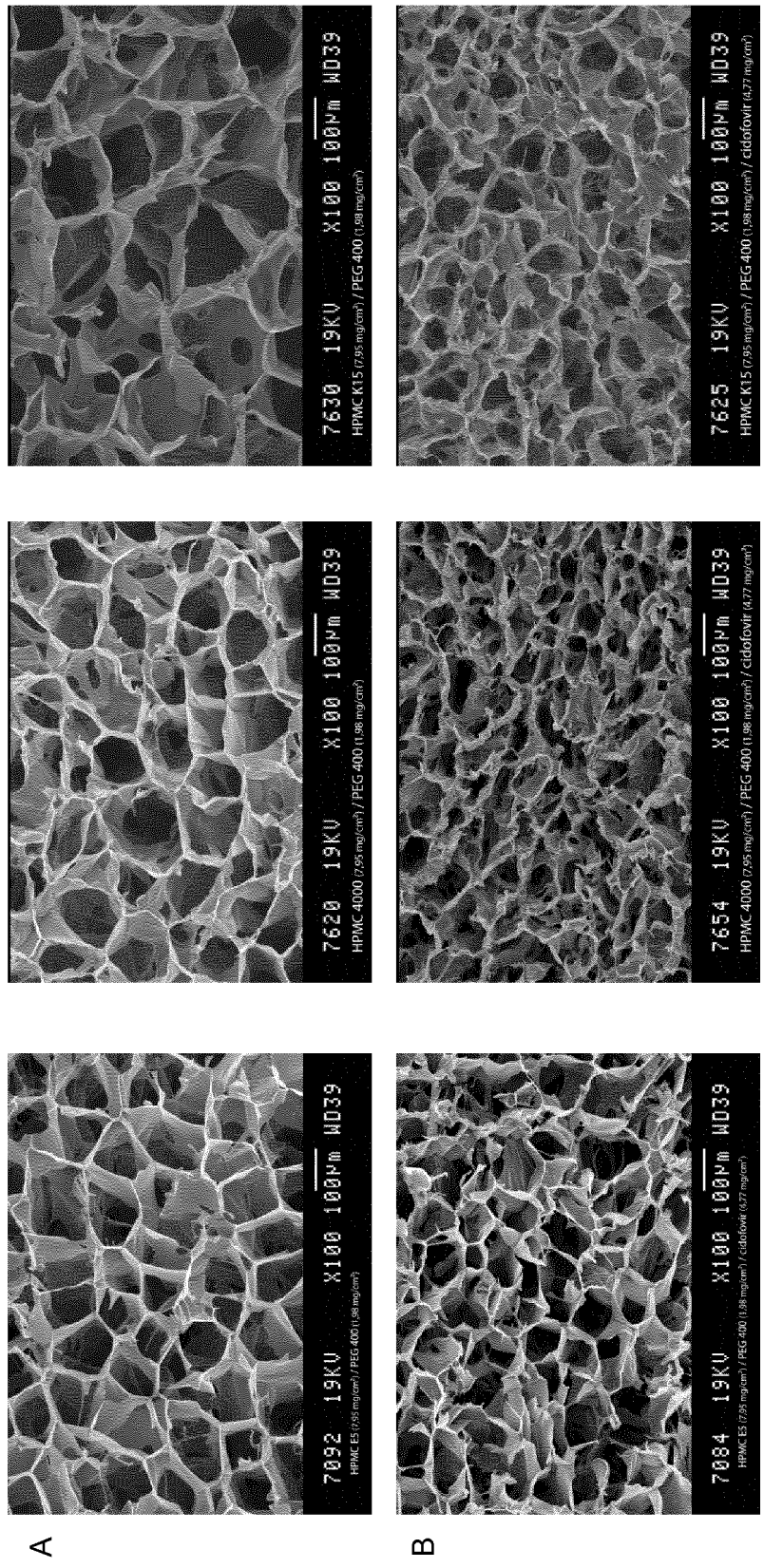
FIG. 9: Scanning electron microscopy (SEM) at 100× magnification of a placebo composition (Row A) or a composition according to an embodiment of the disclosure (Row B) comprising HPMC E5 (left image) or HPMC 4000 (middle image) or HPMC K15 (right image) as polymer.

FIGS. 4 through 8 are pictures of HPMC E5-based sponges at different magnitudes. From FIG. 4, it is apparent that the external layer of PG-based sponges have more grooves than PEG 400-based sponges. From FIG. 5, it is apparent that the pores are better organized in PEG 400-based sponges than in PG-based sponges. In confirmation that PEG 400-based sponges are more resistant, PG appears to lead to a disorganization of the pore structure, which pores become more fragile. The addition of cidofovir to the sponges likewise appears to make the pore structure more fragile. From FIG. 6, it appears that the pore surface is smooth in the placebo sponges, whereas the surface is granular in sponges containing cidofovir, irrespective of whether PEG 400 or PG is used as plasticizer. It appears that cidofovir is distributed uniformly. From FIG. 7, it is apparent that an increase in polymer concentration (from 7.95 to 15.91 mg/cm$^2$ HPMC E5) results in a more dense sponge structure with smaller pores. From FIG. 8, it appears that the pore structure is better organized in the presence of PEG 400 plasticizer. In addition, it appears that less grooves are observed on the external layer of the sponge and that the pores are smaller by augmenting the concentration of the PEG 400 plasticizer. FIG. 9 shows scanning electron microscopy images of sponges based on HPMC E5, HPMC 4000 or HPMC K15, with or without cidofovir. The molecular weight of the HPMC polymer appears to affect the pore size: the pores increase with the molecular weight of the polymer. Smaller pores are observed in the presence of cidofovir. The presence of cidofovir also results in less organized pores, which is even more pronounced in the sponges based on a higher molecular weight HPMC polymer.

Figure 10:
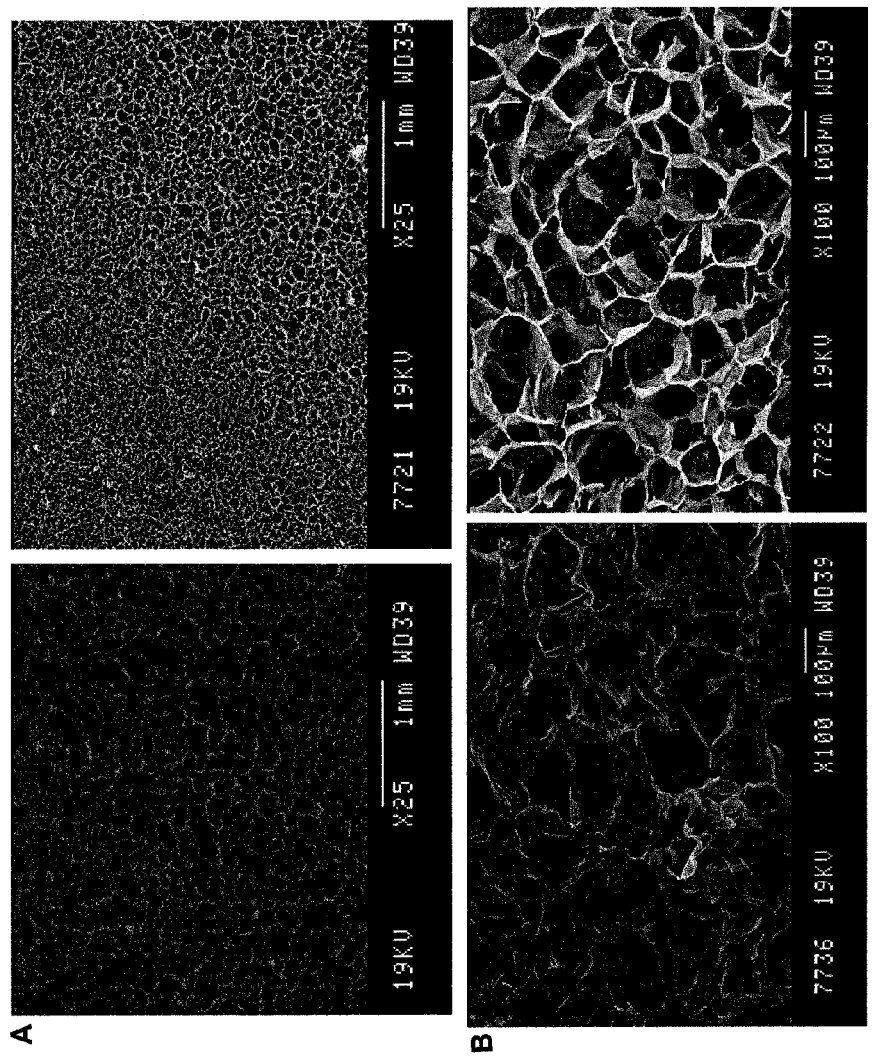
FIG. 10: Scanning electron microscopy (SEM) of compositions comprising HEC 250HX. (Row A) SEM at 25× magnification of the external layer of a placebo composition comprising 1.98 mg/cm² of PEG 400 as plasticizer (left image) or a composition according to an embodiment of the disclosure comprising 1.98 mg/cm² of PEG 400 as plasticizer (right image). (Row B) SEM at 100× magnification of a placebo composition comprising 1.98 mg/cm² of PEG 400 as plasticizer (left image) or a composition according to an embodiment of the disclosure comprising 1.98 mg/cm² of PEG 400 as plasticizer (right image).
Figure 11:
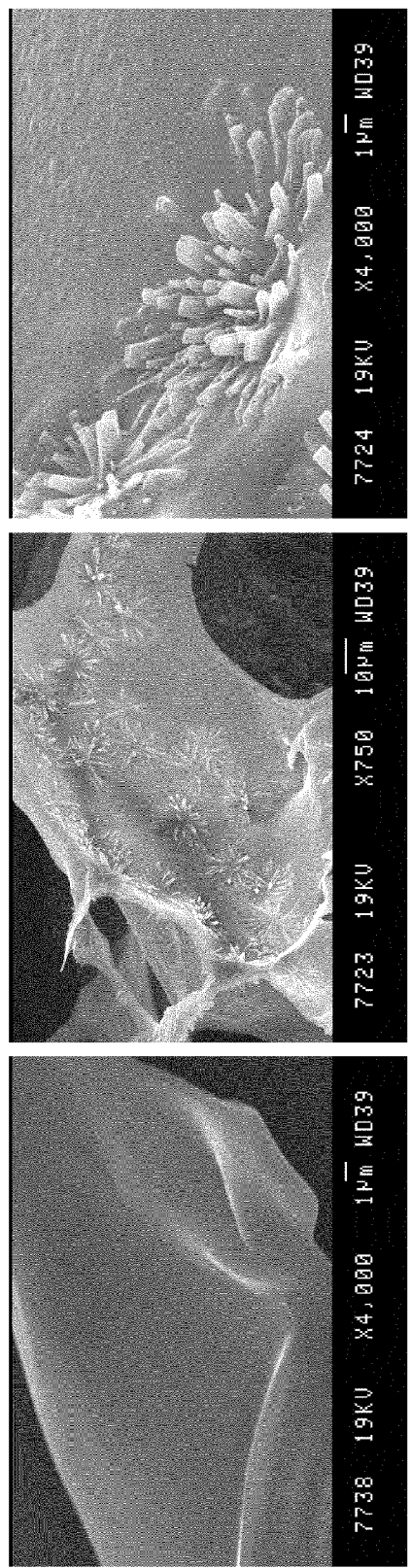
FIG. 11: Scanning electron microscopy (SEM) of compositions comprising HEC 250HX as polymer. SEM of a placebo composition at 4000× magnification (left image) or a composition according to an embodiment of the disclosure at 750× magnification (middle image) or a composition according to an embodiment of the disclosure at 4000× magnification (right image), each comprising PEG 400 as a plasticizer.

FIGS. 10 and 11 represent pictures of sponges based on HEC 250HX polymer. From FIG. 10, it seems that the pores are smaller in the presence of cidofovir. From FIG. 11, it appears that the pore surface is smooth in the placebo sponges, whereas the surface is granular in sponges containing cidofovir. It appears that cidofovir is distributed in crystal form uniformly.

Example 10

Porosity and Sponge Thickness

Experiments have been performed to evaluate the parameters that influence the thickness of the sponge. It has been found that increasing the quantity of the polymer in the aqueous composition before lyophilization only slightly increased the thickness of the sponge after lyophilization. On the other hand, the thickness of the sponge after lyophilization could be increased substantially by increasing the amount of water that is added to the mixture before lyophilization. Thicker sponges were obtained with a mixture of at least 8 g (8, 9, 12, or 15 g). Moreover, it appeared that PG-based compositions allowed for obtaining thicker sponges, whereas PEG 400-based compositions under the same conditions liquefied. A longer lyophilization cycle may be needed.

Example 11

Viscosity

The viscosity of the sponges after rehydration was performed with a rheometer (ARES G2, TA instrument). The following parameters were kept constant for ease of comparison: sponge surface and amount of water for rehydration (900 µl except for FIGS. 14 and 15). Measurements were performed at 37° C. for 240 seconds at a rotation speed from 1 to 100 s$^{-1}$.

Figure 12:
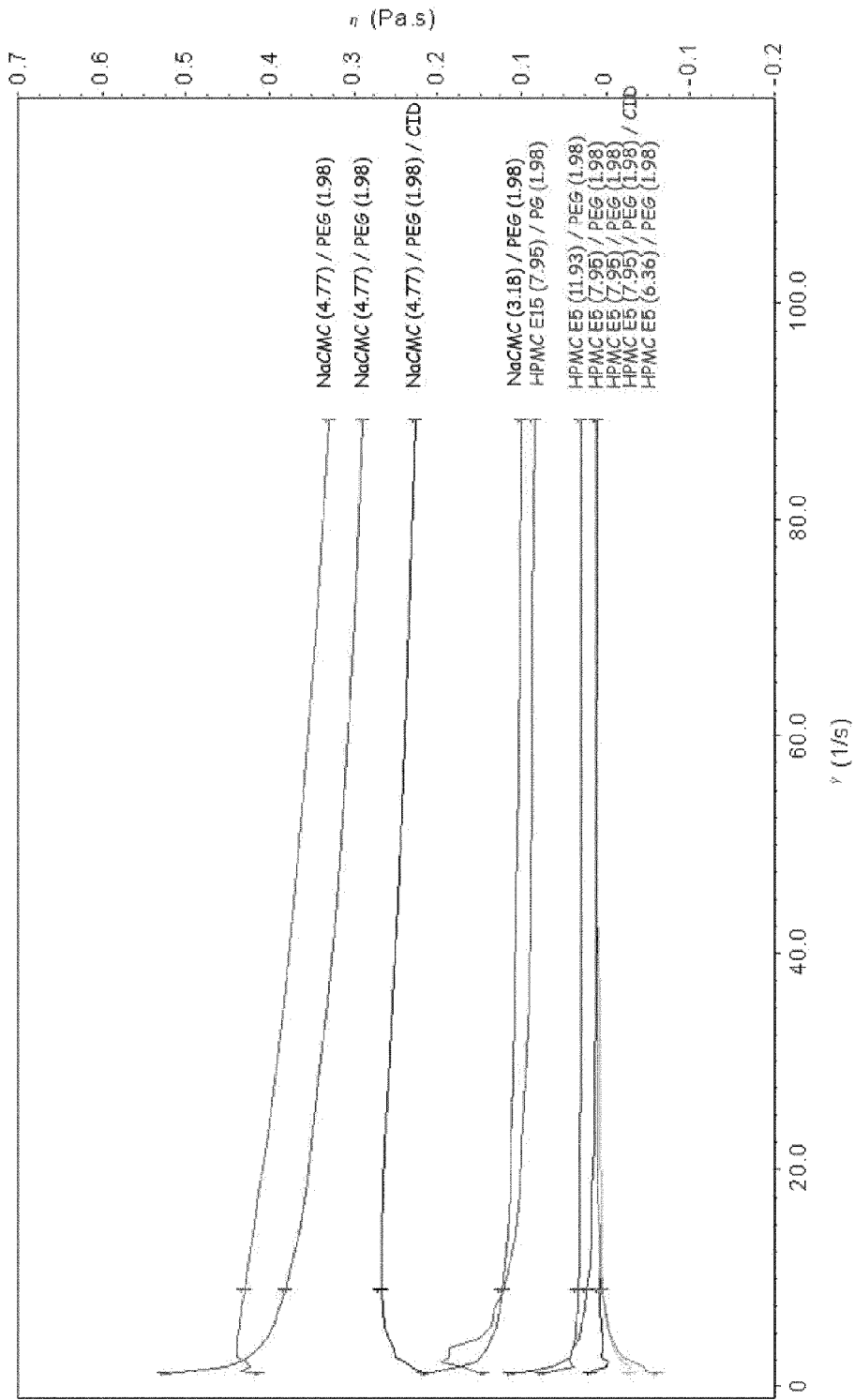
FIGS. 12A and 12B: Viscosity of rehydrated lyophilized compositions comprising NaCMC or compositions comprising HPMC according to an embodiment of the disclosure. Viscosity (Pa·s) is shown in function of rotation speed (s⁻¹). (top graph) general overview; (bottom graph—enlarged on FIG. 12B) detail of the indicated portion in the top graph. The order of the references follows the order of the curve in the figure, starting from the top curve.
Figure 13:
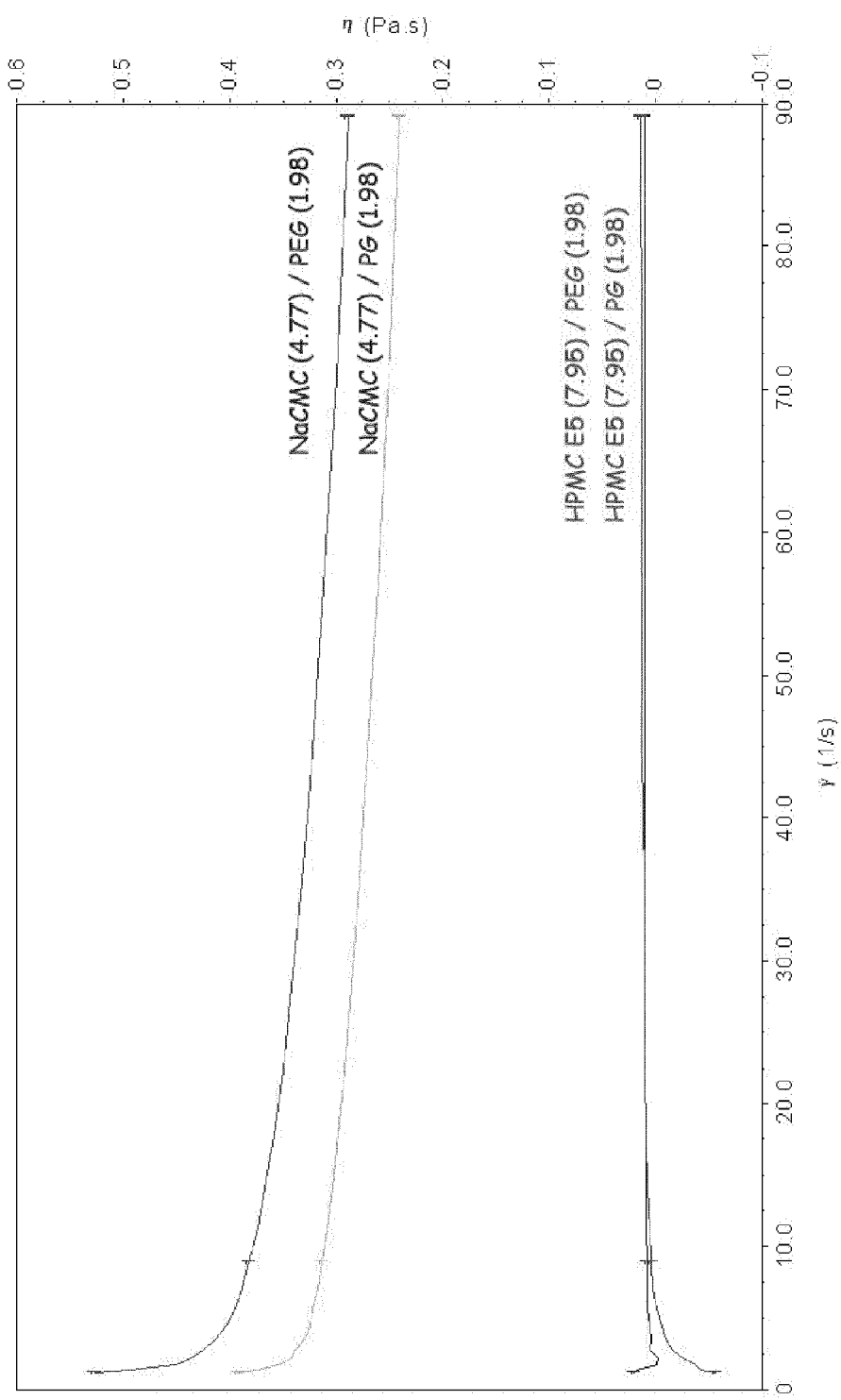
FIG. 13: Viscosity of rehydrated lyophilized compositions comprising NaCMC or compositions comprising HPMC E5 according to an embodiment of the disclosure in function of the plasticizer. Viscosity (Pa·s) is shown in function of rotation speed (s⁻¹). The order of the references follows the order of the curve in the figure, starting from the top curve.

From FIG. 12, it is clear that the NaCMC-based sponges are more viscous than the HPMC E5-based sponges. No difference in viscosity was observed between different HPMC E5 concentrations. HPMC E15-based sponges appeared more viscous than HPMC E5-based sponges (approaching the viscosity of NaCMC-based sponges). From FIG. 13, it is clear that the viscosity is not influenced by the nature of plasticizer (PEG 400 or PG).

Figure 14:
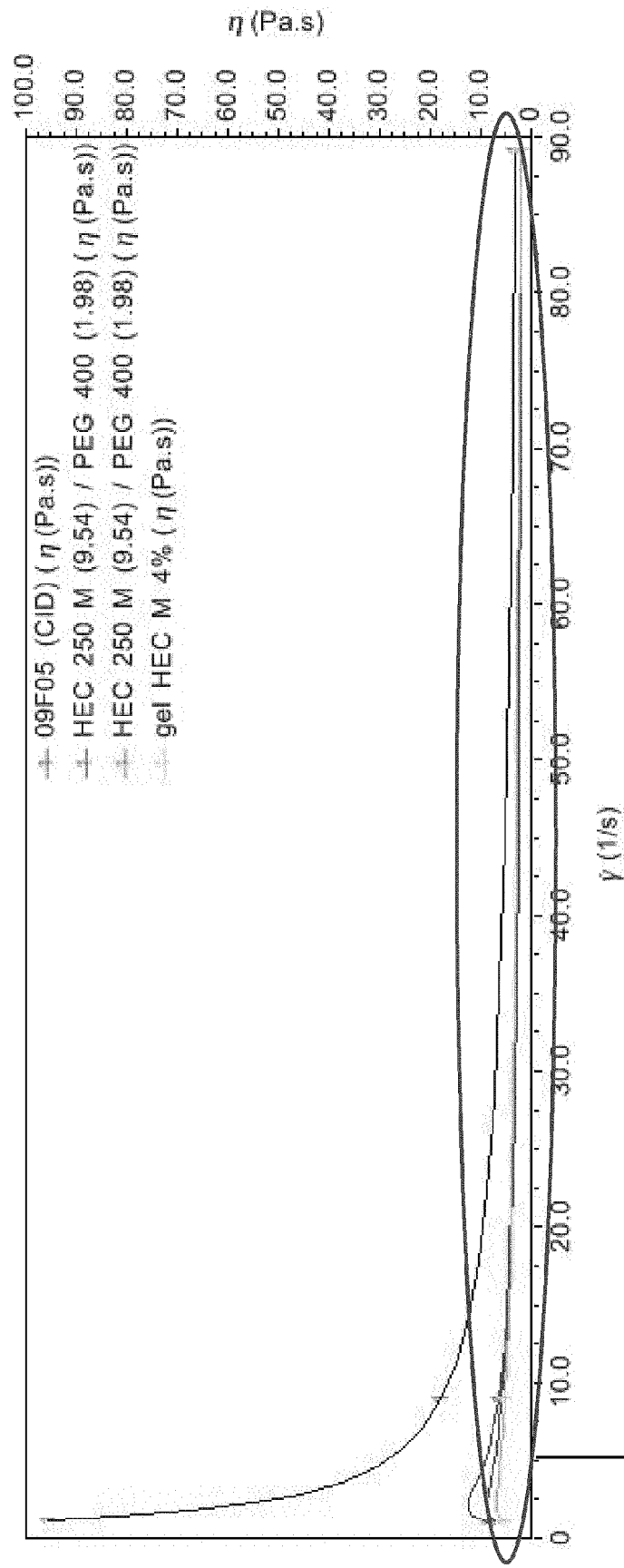
FIGS. 14A and 14B: Comparison of the viscosity of a gel comprising HEC 250M 4% (without lyophilization), a sponge comprising HEC 250M 4% after rehydration with water ad 3 g and a carbomer gel with cidofovir. Vi limited to particular methods, components, products or combinations described, as such methods, components, products and combinations may, of course, vary. It is also to be understood that the terminology used herein is not intended to be limiting.
Figure 14:
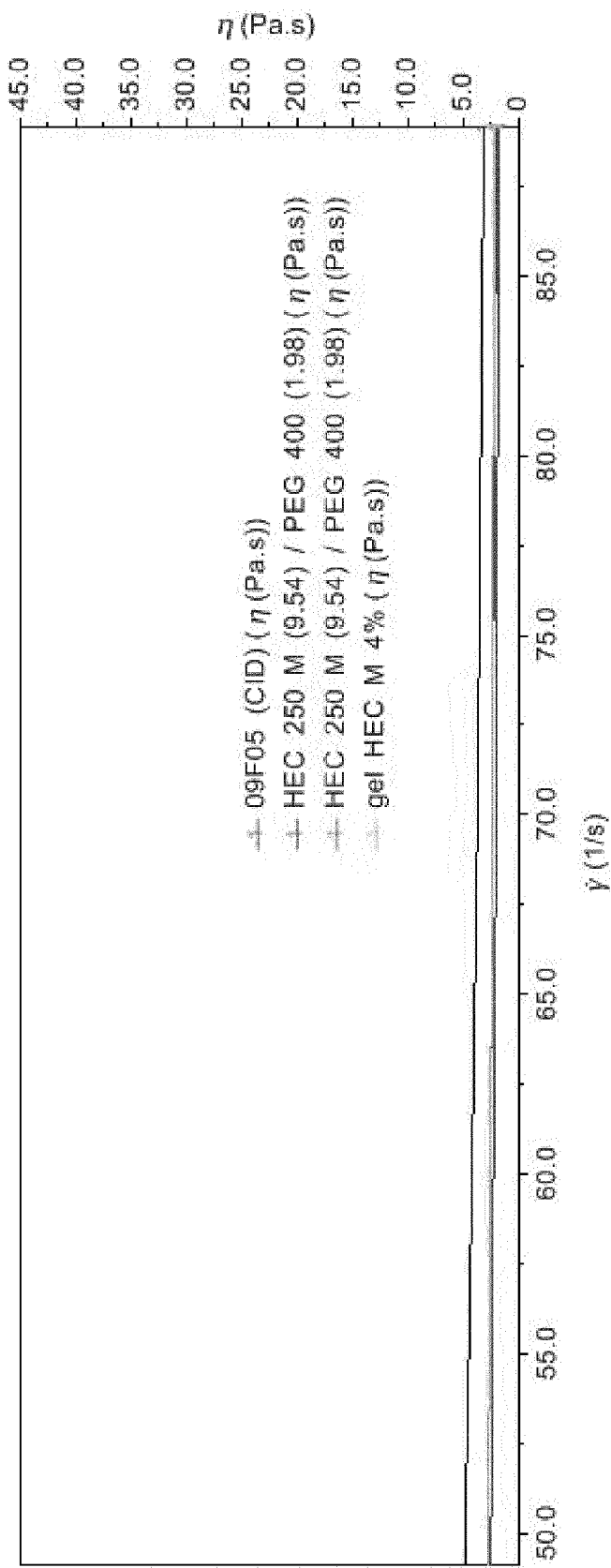
Figure 15:
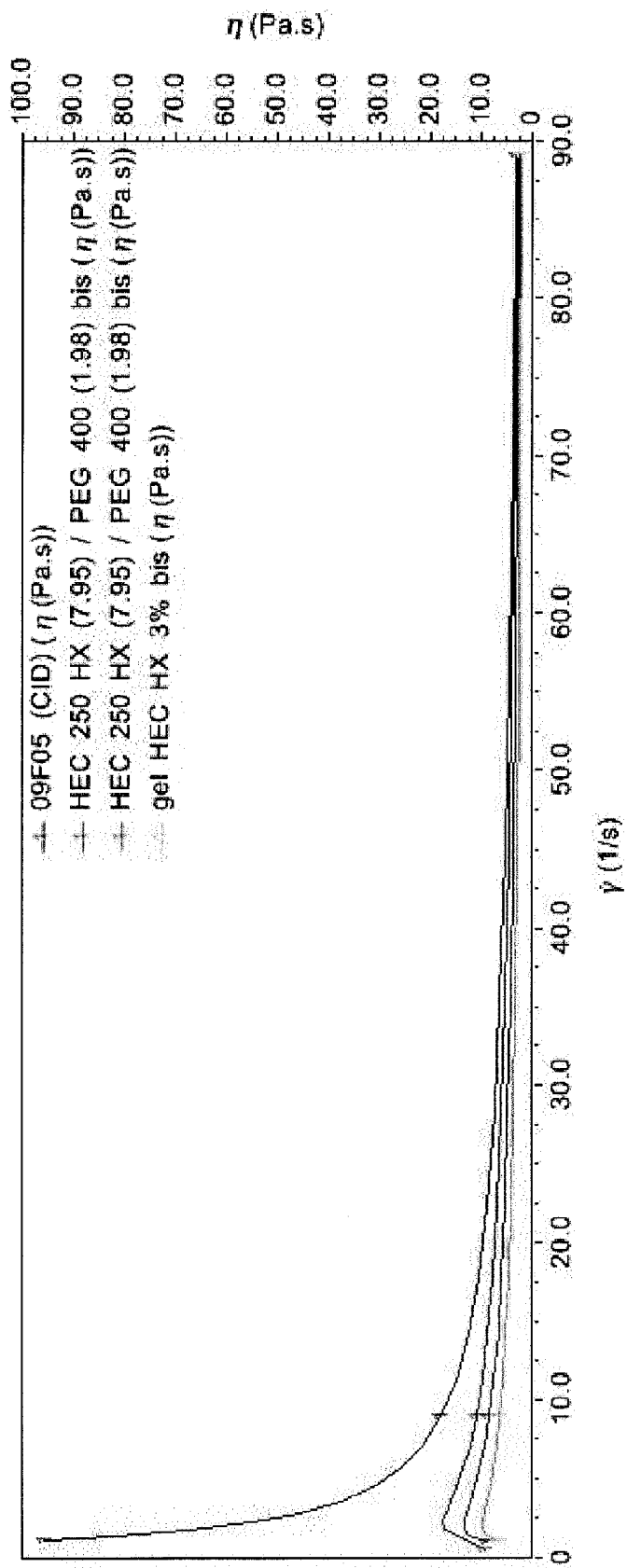
Figure 15:
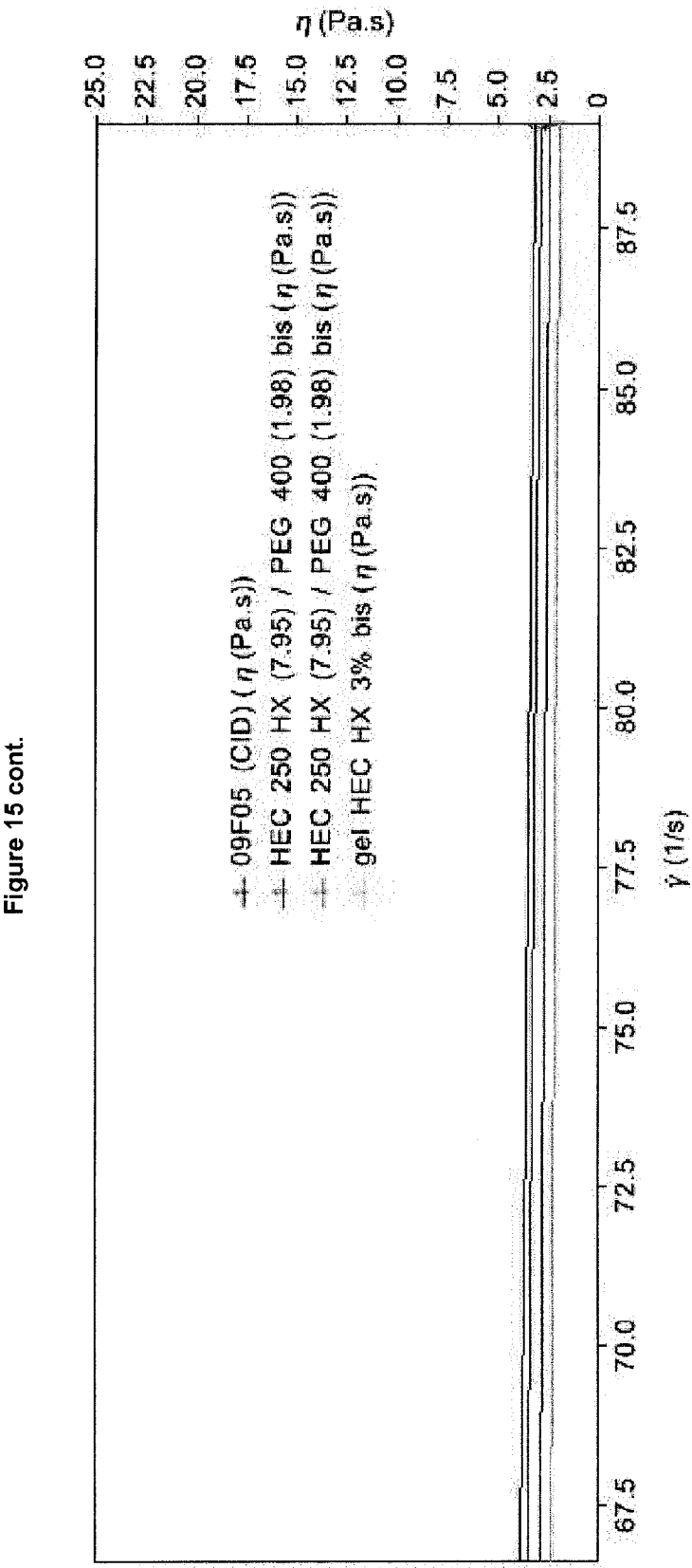

From FIGS. 14 and 15, it appears that the viscosity of the lyophilized compositions is not influenced by the lyophilization process. The viscosity of rehydrated HEC 250 M- and HEC 250 HX-based sponges is comparable to the viscosity of HEC 250 M and HEC 250 HX gels (that were not lyophilized) and approaches the viscosity of a carbomer gel comprising cidofovir.

Figure 16:
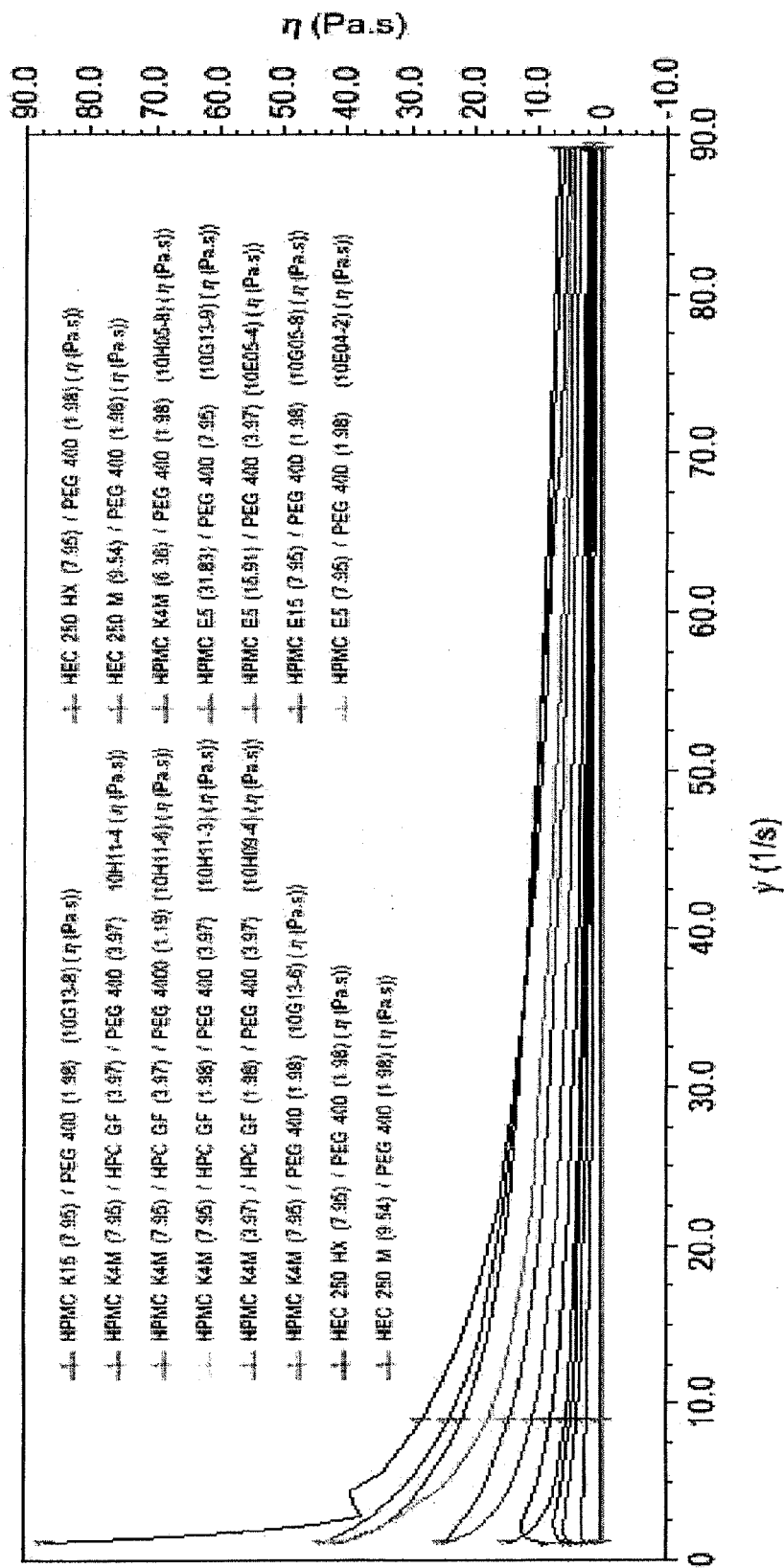
Figure 16:
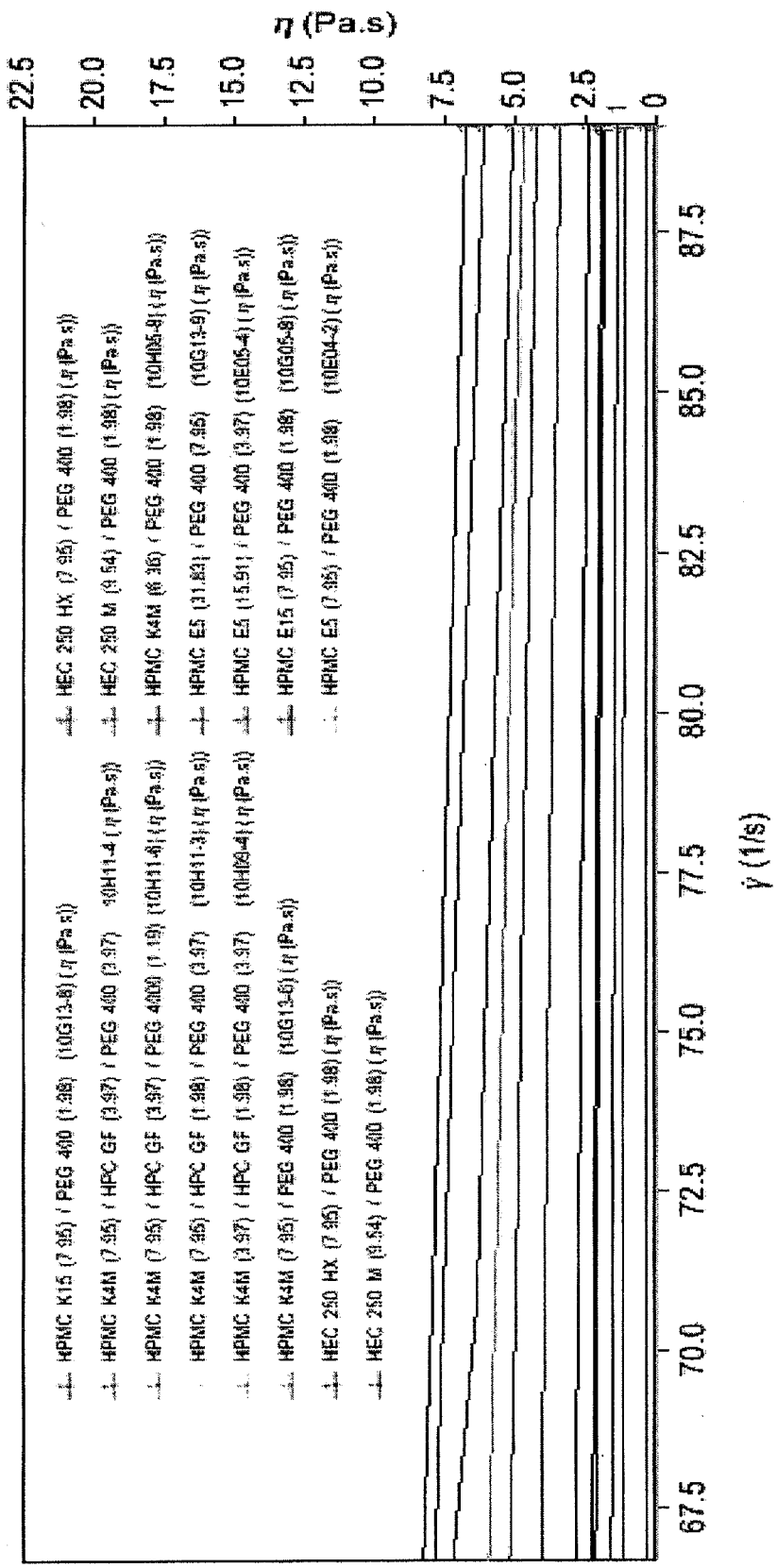

From FIG. 16, it is clear that the viscosity is influenced by the type of polymer: HMPC K15, HPMC 4000 (with or without HPC GF), HEC 250 HX, HEC 250 M, HPMC E15 and HPMC E5 are classified following decreasing viscosity. Furthermore, the viscosity increases with increasing concentration of the polymer.

Example 12

Sponge Measurements by Differential Scanning Calorimetry

Figure 17:
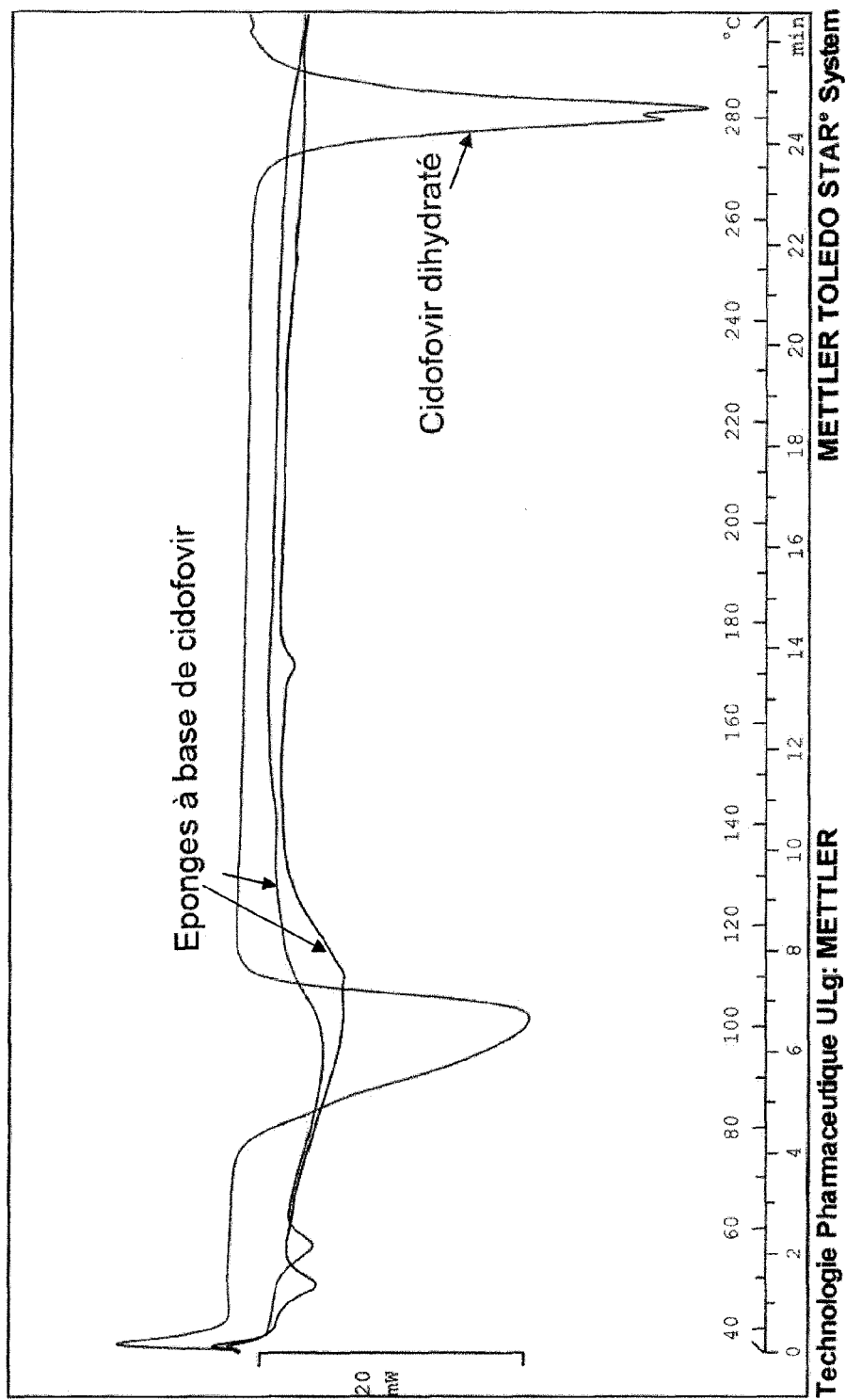

The thermal transitions of lyophilisates and the eventual interaction between the polymers and cidofovir were evaluated by differential scanning calorimetry (DSC 25 Mettler Toledo, controlled by the TC15 TA Controller). The temperature was increased by 10° C. per minute between 35° C. and 300° C. From FIG. 17, it is clear that cidofovir dehydrated in powder form shows an endothermal peak at 280° C. This peak is absent in the calorimetrical analysis of the different sponges because cidofovir is transformed to salt by the method for producing the lyophilized composition.

The invention claimed is:

1. A sheet-shaped lyophilized composition comprising:
   (a) cidofovir in an amount between 0.1 and 5 mg/cm$^2$;
   (b) hydroxyethylcellulose (HEC) or hydroxypropylmethylcellulose (HPMC) in an amount between 1 and 17 mg/cm$^2$; and, optionally,
   (c) a plasticizer in an amount between 0 and 5 mg/cm$^2$.

2. The lyophilized composition of claim 1 comprising:
   (a) cidofovir in an amount between 0.1 and 5 mg/cm$^2$;
   (b) hydroxyethylcellulose (HEC) in an amount between 1 and 17 mg/cm$^2$; and
   (c) a plasticizer in an amount between 0.5 and 4 mg/cm$^2$.

3. The lyophilized composition of claim 1, wherein HEC is present in an amount between 5and-16 mg/cm$^2$.

4. The lyophilized composition of claim 2, wherein said HEC is selected from the group consisting of HEC H4000, HEC 250HHX, HEC 250M, and HEC 250HX.

5. The lyophilized composition of claim 2, which presents itself as a high viscosity composition after rehydration.

6. The lyophilized composition of claim 1 comprising:
   (a) cidofovir in an amount between 0.1 and 5 mg/cm$^2$;
   (b) hydroxypropylmethylcellulose (HPMC) in an amount between 1 and 17 mg/cm$^2$; and
   (c) a plasticizer in an amount between 0 and 5 mg/cm$^2$.

7. The lyophilized composition of claim 6, wherein HPMC is present in an amount between 2.5 and 15 mg/cm$^2$.

8. The lyophilized composition of claim 6, wherein said HPMC is selected from the group consisting of HPMC E5, HPMC E15, HPMC 4000, and HPMC K15.

9. The lyophilized composition of claim 6, which presents itself as a low viscosity composition after rehydration.

10. The lyophilized composition of claim 1, wherein said plasticizer is selected from the group consisting of polyethylene glycol 400 (PEG 400), polyethylene glycol 4000 (PEG 4000) and propylene glycol (PG).

11. The lyophilized composition of claim 1, wherein water is present in an amount between 1 and 10 weight %, and/or NaOH is present in an amount of between 0.15 and 0.25 weight %.

12. The lyophilized composition of claim 1, wherein said composition is a porous malleable matrix.

13. A method of treating a subject diagnosed as being infected with infection with a human DNA virus, the method comprising:
   applying the lyophilized composition of claim 1 to the subject so as to treat infection with the human DNA virus, Herpes virus, Pox virus, Papilloma virus, Adenovirus, Smallpox virus, or Human papillomavirus (HPV), or accompanying pathologies selected from the group consisting of virus-induced lesions or warts of the vagina, cervix, anogenital region, mucosa, epithelium of the oral sphere, or skin, precancerous lesions and/or neoplasms or cancers caused by HPV infection.

14. A gel-like composition obtained after rehydration of the lyophilized composition of claim 1.

15. The method of claim 13, wherein the composition is rehydrated before administration.

16. The method of claim 13, wherein the composition is not rehydrated before administration.

17. The method of claim 13, comprising drug delivery to the subject's vagina, cervix, anogenital region, mucosa, epithelium of the oral sphere, or skin.

18. A method for producing the lyophilized composition of claim 1, comprising the steps of:
   (a) dispersing HEC or HPMC in water to obtain a homogenized composition;
   (b) optionally dispersing plasticizer in the composition obtained in step (a) to obtain a homogenized composition;
   (c) dispersing cidofovir and optionally adding NaOH 2M solution in the composition obtained in step (b) or, alternatively, the composition obtained in step (a) if no plasticizer is added to obtain a homogenized composition; and
   (d) lyophilizing the composition obtained in step (c), wherein plasticizer needs to be added in step (b) when HEC is used in step (a).

19. The method of claim 18, wherein the homogenized composition of step (c) comprises between 1 and 17 mg/cm$^2$ of HEC or HPMC.

20. The method of claim 17, wherein the homogenized composition of step (c) comprises between 5 and 16 mg/cm$^2$ HEC and between 1.5 and 33 mg/cm$^2$ plasticizer.

21. The method of claim 17, wherein the homogenized composition of step (c) comprises between 2.5 and 8 mg/cm$^2$, between 4 and 8 mg/cm$^2$, or between 8 and 15 mg/cm$^2$ HPMC and between 0 and 5 mg/cm$^2$ plasticizer.

22. The method of claim 17, wherein the homogenized composition of step (c) comprises between 0.1 and 5 mg/cm$^2$ cidofovir.

23. The method of claim 17, wherein the homogenized composition of step (c) has a pH between 6 and 8.

24. The method of claim 23, wherein the homogenized composition of step (c) comprises NaOH.

25. A method of preparing a gel-like composition, the method comprising the step of rehydrating the lyophilized composition of claim 1.

26. A sheet-shaped solid porous malleable matrix obtained by lyophilization of an aqueous composition, said aqueous composition comprising between 1 and 17 mg/cm$^2$ HEC or HPMC, between 0 and 5 mg/cm$^2$ plasticizer, and between 0.1 and 5 mg/cm$^2$ cidofovir, wherein between 1.5 and 3 mg/cm$^2$ of said plasticizer is present when HEC is used.

27. The matrix of claim 25, wherein said aqueous composition comprises:
   between 5 and 16 mg/cm$^2$ HEC,
   between 1.5 and 3 mg/cm$^2$ plasticizer, and
   between 0.1 and 5 mg/cm$^2$ cidofovir.

28. The matrix of claim 25, wherein said aqueous composition comprises:
   between 2.5 and 15 mg/cm$^2$ HPMC,
   between 0 and 5 mg/cm$^2$ plasticizer, and
   between 0.1 and 5 mg/cm$^2$ cidofovir.

29. A drug delivery applicator, comprising the sheet-shaped lyophilized composition of claim 1.

30. The drug delivery applicator of claim 28, in the form of a cervical cap or a cervix-covering pessary, optionally comprising a drug-impermeable barrier preventing active ingredient from diffusing therefrom, or in the form of a vaginal inserter, a vaginal cream inserter, or a tampon inserter.

31. The method according to claim 13, wherein the lyophilized composition is applied to the cervix or the mucosal surface of the cervix.

* * * * *